(12) United States Patent
Lim et al.

(10) Patent No.: US 8,384,074 B2
(45) Date of Patent: Feb. 26, 2013

(54) HETEROCYCLIC COMPOUND AND ORGANIC LIGHT-EMITTING DEVICE INCLUDING THE SAME

(75) Inventors: Jin-O Lim, Yongin (KR); Seok-Hwan Hwang, Yongin (KR); Young-Kook Kim, Yongin (KR); Yoon-Hyun Kwak, Yongin (KR); Hye-Jin Jung, Yongin (KR); Jong-Hyuk Lee, Yongin (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 72 days.

(21) Appl. No.: 13/078,080

(22) Filed: Apr. 1, 2011

(65) Prior Publication Data

US 2011/0240978 A1   Oct. 6, 2011

(30) Foreign Application Priority Data

Apr. 6, 2010  (KR) .................. 10-2010-0031553

(51) Int. Cl.
*H01L 51/00* (2006.01)
(52) U.S. Cl. .................. 257/40; 257/103; 257/E51.026; 257/E51.028; 428/690
(58) Field of Classification Search .................... 257/40, 257/103, E51.026, E51.028; 428/690
See application file for complete search history.

(56) References Cited

U.S. PATENT DOCUMENTS

| | | | |
|---|---|---|---|
| 3,291,771 | A | 12/1966 | Altermatt |
| 5,645,948 | A | 7/1997 | Shi et al. |
| 5,972,247 | A | 10/1999 | Shi et al. |
| 6,465,115 | B2 | 10/2002 | Shi et al. |
| 6,596,415 | B2 | 7/2003 | Shi et al. |
| 7,989,644 | B2 * | 8/2011 | Tanabe et al. ............. 549/460 |
| 8,247,089 | B2 | 8/2012 | Otsu et al. |
| 2004/0076853 | A1 | 4/2004 | Jarikov |
| 2006/0210830 | A1 | 9/2006 | Funahashi et al. |
| 2007/0155991 | A1 | 7/2007 | Funahashi |
| 2008/0124455 | A1 | 5/2008 | Shin et al. |
| 2008/0203905 | A1 | 8/2008 | Je et al. |
| 2008/0268283 | A1 | 10/2008 | Funahashi |
| 2008/0306303 | A1 | 12/2008 | Rostovtsev et al. |
| 2009/0096393 | A1 | 4/2009 | Taniguchi et al. |

FOREIGN PATENT DOCUMENTS

| | | |
|---|---|---|
| JP | 05-339565 | 12/1993 |
| JP | 1993-339565 A | 12/1993 |
| JP | 1996-012600 | 1/1996 |
| JP | 2000-003782 | 7/2000 |
| JP | 2006-052324 A | 2/2006 |
| JP | 2008-078362 A | 4/2008 |
| JP | 2008-218987 A | 9/2008 |
| JP | 2008-290999 A | 12/2008 |
| JP | 2010-073987 A | 4/2010 |
| KR | 2011-0039108 A | 4/2011 |
| WO | 2008-150872 A1 | 12/2008 |
| WO | 2009-008354 | 1/2009 |
| WO | 2010-053210 A1 | 5/2010 |
| WO | 2010-114264 A2 | 7/2010 |

OTHER PUBLICATIONS

Hwang et al. "Highly efficient and versatile synthesis of polarylfluorenes via pd-catalyzed c-h bond activation." Organic Letters. vol. 11, No. 20 (4588-4591), (2009).

Henriques et al. "Characterization of the coke formed during o-xylene isomerization over mordenites at various tempereatures." Journal of Catalysis 172 (436-445), (Jul. 1997).

Liu et al. "Facile synthesis of spirocyclic aromatic hydrocarbon derivatives based on o-halobiaryl route and domino reaction for deep-blue organic semiconductors." Organic Letters. vol. 11, No. 17 (3850-3853), (2009).

\* cited by examiner

*Primary Examiner* — Tu-Tu Ho
(74) *Attorney, Agent, or Firm* — Robert E. Bushnell, Esq.

(57) ABSTRACT

A heterocyclic compound of formula 1 and an organic light-emitting device including an organic layer containing the heterocyclic compound. The heterocyclic compound of Formula 1 may be suitable as a material for an emission layer, an electron transport layer or an electron injection layer of an organic light-emitting device. Due to the inclusion of the heterocylic group in its molecular structure, the heterocyclic compound of Formula 1 may have a high glass transition temperature (Tg) or a high melting point, and may prevent crystallization. An organic light-emitting device manufactured using the heterocyclic compound of Formula 1, in which a chrysene group and an indole group are fused, has excellent durability when stored or operated.

20 Claims, 2 Drawing Sheets

HETEROCYCLIC COMPOUND AND ORGANIC LIGHT-EMITTING DEVICE INCLUDING THE SAME

CLAIM OF PRIORITY

This application claims the benefit of Korean Patent Application No. 10-2010-0031553, filed on Apr. 6, 2010, in the Korean Intellectual Property Office, the disclosure of which is incorporated herein in its entirety by reference.

BACKGROUND OF THE INVENTION

1. Field of the Invention

The present invention relates to a heterocyclic compound and an organic light-emitting device including the heterocyclic compound.

2. Description of the Related Art

Organic light-emitting devices are self-emitting display devices and have a wide viewing angle, a high contrast ratio, and a short response time. Due to these characteristics, organic light-emitting devices are drawing more attention.

Typically, an organic light-emitting device has a stack structure including an anode, a cathode and an organic emission layer interposed there between. However, a hole injection layer and/or a hole transport layer may be further stacked between the anode and the organic emission layer, and an electron transport layer may be further stacked between the organic emission layer and the cathode. In other words, an organic light-emitting device may have a stack structure of anode/hole transport layer/organic emission layer/cathode or a stack structure of anode/hole transport layer/organic emission layer/electron transport layer/cathode.

As a material for the organic emission layer, an anthracene derivative can be used. However, organic light-emitting devices including such a known organic emission material do not have satisfactory life span, efficiency, and power consumption characteristics, still leaving a demand for further improvement.

SUMMARY OF THE INVENTION

The present invention provides a heterocyclic compound having improved electrical characteristics, charge transporting capability and light-emission capability.

The present invention provides an organic light-emitting device including a heterocyclic compound.

According to an aspect of the present invention, there is provided a heterocyclic compound represented by Formula 1 below:

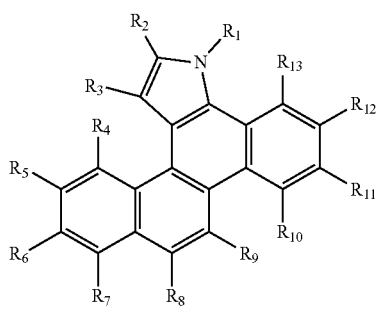

Formula 1

In Formula 1, $R_1$ through $R_{13}$ are each independently selected from the group consisting of a hydrogen atom, a deuterium atom., a halogen atom, a cyano group, an amino group, a nitro group, a hydroxyl group, a carboxyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_3$-$C_{50}$ cycloalkyl group, a substituted or unsubstituted $C_1$-$C_{50}$ alkoxy group, a group represented by —$(Ar_1)_a$—$(Ar_{11})$, and a group represented by —N[—$(Ar_2)_b$—$(Ar_{12})$][—$(Ar_3)_c$—$(Ar_{13})$], wherein at least two adjacent groups of $R_1$ through $R_{13}$ are linked to form a saturated or unsaturated ring;

$Ar_1$ through $Ar_3$ are each independently selected from the group consisting of a substituted or unsubstituted $C_1$-$C_{50}$ alkylene group, a substituted or unsubstituted $C_2$-$C_{50}$ alkenylene group, a substituted or unsubstituted $C_5$-$C_{60}$ arylene group, and a substituted or unsubstituted $C_4$-$C_{60}$ heteroarylene group;

$Ar_{11}$, $Ar_{12}$ and $Ar_{13}$ are each independently selected from the group consisting of a substituted or unsubstituted $C_5$-$C_{60}$ aryl group, a substituted or unsubstituted $C_5$-$C_{50}$ aryloxy group, a substituted or unsubstituted $C_5$-$C_{50}$ arylthio group, and a substituted or unsubstituted $C_4$-$C_{60}$ heteroaryl group;

a, b and c are each independently an integer from 0 to 10; and

"a" groups of —$Ar_1$— in —$(Ar_1)_a$—$(Ar_{11})$ are identical to or different from each other, "b" groups of —$Ar_2$— in —N[—$(Ar_2)_b$—$(Ar_{12})$][—$(Ar_3)_c$—$(Ar_{13})$] are identical to or different from each other, and "c" groups of —$Ar_3$— are identical to or different from each other.

The heterocyclic compound may be represented by Formula 2 below:

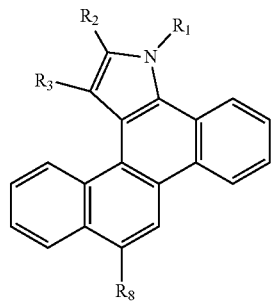

Formula 2

In Formula 2, $R_1$, $R_2$, $R_3$ and $R_8$ are each independently selected from the group consisting of a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_3$-$C_{50}$ cycloalkyl group, a substituted or unsubstituted $C_1$-$C_{50}$ alkoxy group, a group represented by —$(Ar_1)_a$—$(Ar_{11})$, and a group represented by —N[—$(Ar_2)_b$—$(Ar_{12})$][—$(Ar_3)_c$—$(Ar_{13})$], wherein at least two adjacent groups of $R_1$ through $R_3$ are linked to form a saturated or unsaturated ring; and $Ar_1$, $Ar_2$, $Ar_3$, $Ar_{11}$, $Ar_{12}$, $Ar_{13}$, a, b and c are defined as described above in conjunction with Formula 1.

According to another aspect of the present invention, there is provided an organic light-emitting device including: a first electrode; a second electrode disposed opposite to the first electrode; and an organic layer disposed between the first electrode and the second electrode, the organic layer containing the heterocyclic compound described above.

BRIEF DESCRIPTION OF THE DRAWING

A more complete appreciation of the invention, and many of the attendant advantages thereof, will be readily apparent as the same becomes better understood by reference to the following detailed description when considered in conjunction with the accompanying drawings in which like reference symbles indicate the same or similar components, wherein.

DETAILED DESCRIPTION OF THE INVENTION

Figure 1:
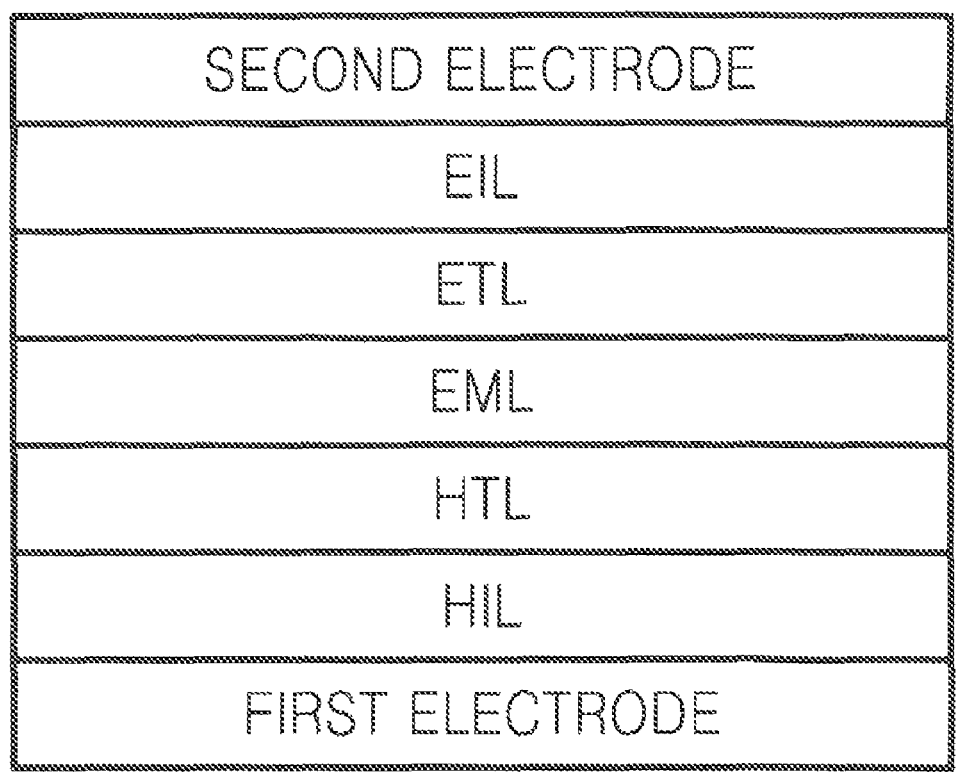
FIG. 1 illustrates the structure of an organic light-emitting device according to an embodiment of the present invention.
Figure 2:
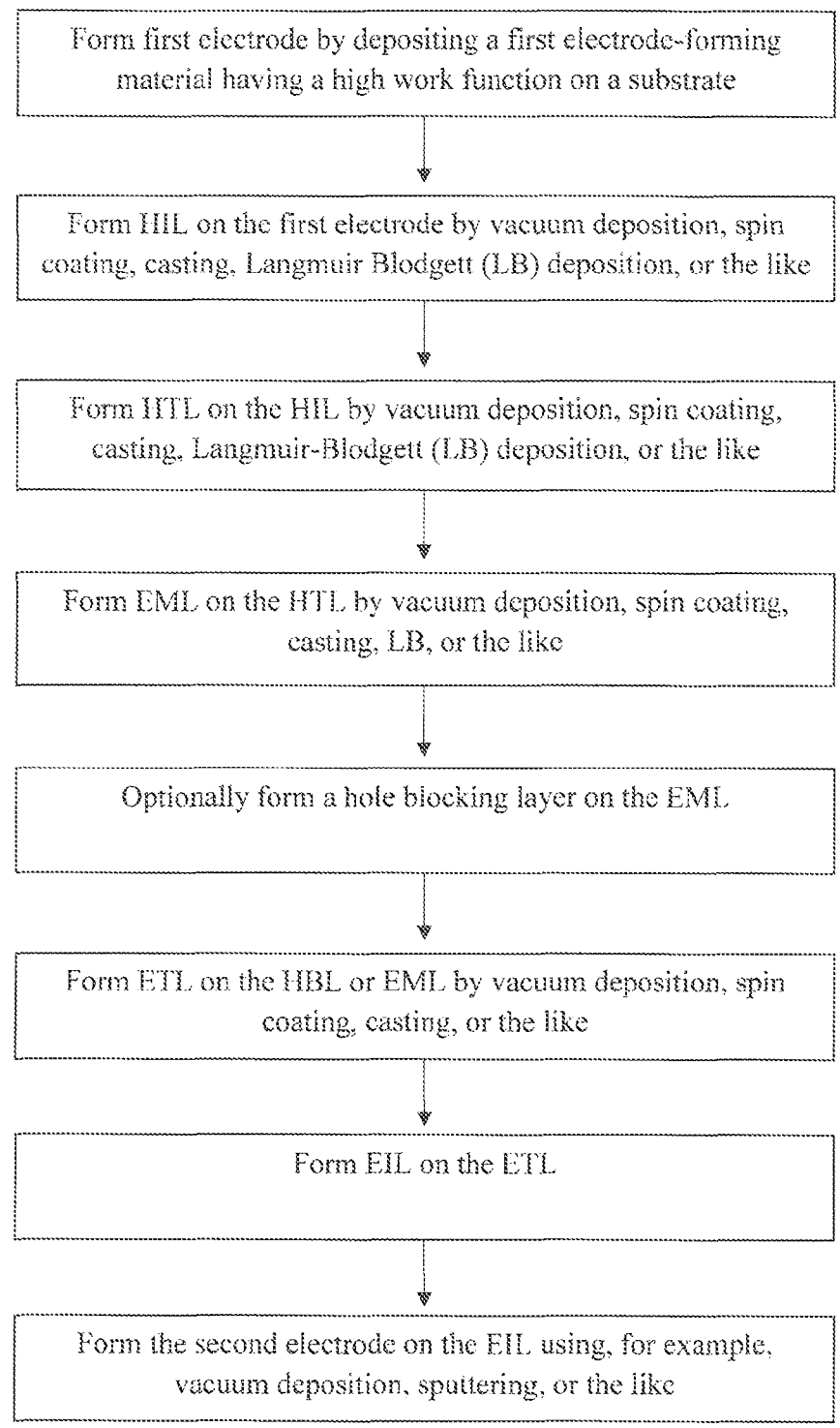
FIG. 2 is a flowchart which shows a process for making an organic light emitting device according to an embodiment if the present invention.

A heterocyclic compound according to an embodiment of the present invention is represented by Formula 1 below:

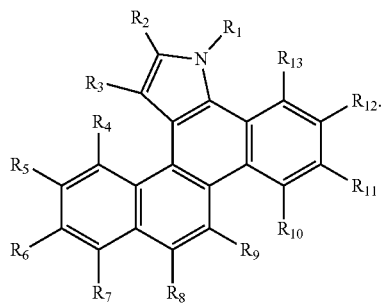

Formula 1

In Formula 1 above, $R_1$ through $R_{13}$ are each independently selected from the group consisting of a hydrogen atom, a deuterium atom, a halogen atom, a cyano group, an amino group, a nitro group, a hydroxyl group, a carboxyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_3$-$C_{50}$ cycloalkyl group, a substituted or unsubstituted $C_1$-$C_{50}$ alkoxy group, a group represented by —$(Ar_1)_a$—$(Ar_{11})$, and a group represented by —$N[-(Ar_2)_b-(Ar_{12})][-(Ar_3)_c-(Ar_{13})]$, wherein at least two adjacent groups of $R_1$ through $R_{13}$ may be linked to form a saturated or unsaturated ring.

$Ar_1$ through $Ar_3$ are each independently selected from the group consisting of a substituted or unsubstituted $C_1$-$C_{50}$ alkylene group, a substituted or unsubstituted $C_2$-$C_{50}$ alkenylene group, a substituted or unsubstituted $C_5$-$C_{60}$ arylene group, and a substituted or unsubstituted $C_4$-$C_{60}$ heteroarylene group;

$Ar_1$ through $Ar_3$ may be each independently selected from the group consisting of a substituted or unsubstituted $C_5$-$C_{20}$ arylene group and a substituted or unsubstituted $C_4$-$C_{20}$ heteroarylene group.

Examples of the substituted or unsubstituted $C_5$-$C_{20}$ arylene group and the substituted or unsubstituted $C_4$-$C_{20}$ heteroarylene group include, but are not limited to, a phenylene group, a $C_1$-$C_{10}$ alkylphenylene group, a $C_1$-$C_{10}$ alkoxyphenylene group, a halophenylene group, a cyanophenylene group, a dicyanophenylene group, a trifluoromethoxyphenylene group, an o-, m-, or p-tolylene group, an o-, m- or p-cumenylene group, a mesitylene group, a phenoxyphenylene group, a (α,α-dimethylbenzene)phenylene group, a ($C_1$-$C_{10}$ alkylcyclohexyl)phenylene group, a (anthracenyl) phenylene group, a biphenylene group, a $C_1$-$C_{10}$ alkylbiphenylene group, a $C_1$-$C_{10}$ alkoxybiphenylene group, a pentalenyl group, an indenylene group, a naphthylene group, a $C_1$-$C_{10}$ alkylnaphthylene group, a $C_1$-$C_{10}$ alkoxynaphthylene group, a halonaphthylene group, a cyanonaphthylene group, a biphenyllenylene group, a $C_1$-$C_{10}$ alkyl biphenyllenylene group, a $C_1$-$C_{10}$ alkoxy biphenyllenylene group, a biphenylanthracenylene group, an anthracenylene group, an azulenylene group, a heptalenylene group, an acenaphthyllenylene group, a phenalenylene group, a fluorenylene group, an anthraquinolylene group, a methylanthrylene group, a phenanthrenylene group, a triphenyllenylene group, a pyrenylene group, a chrysenylene group, an ethylchrysenylene group, a picenylene group, a perylenylene group, a chloroperylenylene group, a pentaphenylene group, a pentacenylene group, a tetraphenyllenylene group, a hexaphenylene group, a hexacenylene group, a rubicenylene group, a coronenylene group, a trinaphthyllenylene group, a heptaphenylene group, a heptacenylene group, a pyranthrenylene group, an ovalenylene group, a carbazolylene group, a $C_1$-$_{10}$ alkyl carbazolylene group, a thiophenylene group, an indolylene group, a purinylene group, a benzimidazolylene group, a quinolinylene group, a benzothiophenylene group, a parathiazinylene group, a pyrrolylene group, a pyrazolylene group, an imidazolylene group, an imidazolinylene group, an oxazolylene group, a thiazolylene group, a triazolylene group, a tetrazolylene group, an oxadiazolyl group, a pyridinylene group, a pyridazinylene group, a pyrimidinylene group, a pyrazinylene group, a thianthrenylene group, a pyrrolidinylene group, a pyrazolidinylene group, an imidazolidinylene group, a piperidinylene group, a piperazinylene group, and a morpholinylene group.

For example, $Ar_1$ through $Ar_3$ may be each independently selected from the group consisting of a phenylene group, a $C_1$-$C_{10}$ alkyl phenylene group, a di($C_1$-$C_{10}$ alkyl) phenylene group, a naphthylene group, a $C_1$-$C_{10}$ alkyl naphthylene group, a di($C_1$-$C_{10}$ alkyl) naphthylene group, an anthrylene group, a $C_1$-$C_{10}$ alkyl anthrylene group, a di($C_1$-$C_{10}$ alkyl) anthrylene group, a fluorenylene group, a $C_1$-$C_{10}$ alkyl fluorenylene group, a di($C_1$-$C_{10}$ alkyl) fluorenylene group, a $C_6$-$C_{14}$ aryl fluorenylene group, a di($C_6$-$C_{14}$ aryl) fluorenylene group, a pyridylene group, a $C_1$-$C_{10}$ alkyl pyridylene group, a di($C_1$-$C_{10}$ alkyl) pyridylene group, a carbazolylene group, a $C_1$-$C_{10}$ alkyl carbazolylene group, and a di($C_1$-$C_{10}$ alkyl) carbazolylene group.

For example, $Ar_1$ through $Ar_3$ may be each independently selected from the group consisting of compounds represented by Formulae 2A through 2G below, but are not limited is thereto:

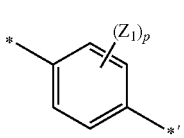

Formula 2A

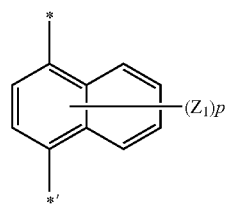

Formula 2B

Formula 2C

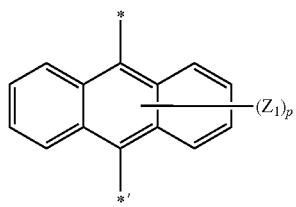

Formula 2D

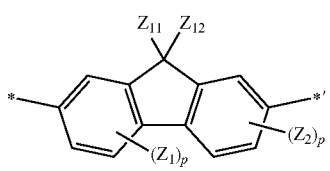

Formula 2E

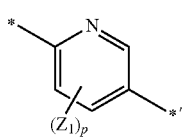

Formula 2F

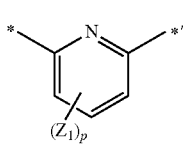

Formula 2G

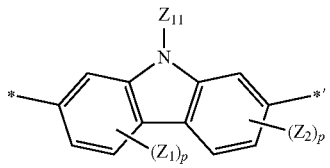

In the formulae above, $Z_1$, $Z_2$, $Z_{11}$ and $Z_{12}$ are each independently selected from the group consisting of a hydrogen atom, a deuterium atom, a $C_1$-$C_{10}$ alkyl group (for example, methyl, ethyl, propyl, isobutyl, sec-butyl or the like), a $C_1$-$C_{10}$ alkoxy group (for example, methoxy, ethoxy, propoxy, isopropyloxy, butoxy or the like), and a $C_6$-$C_{14}$ aryl group (for example, phenyl, naphthyl or the like); p is an integer from 1 to 8; and * denotes a binding site with $Ar_{11}$, $Ar_{12}$, or $Ar_{13}$; and *' denotes a binding site with a ring of the backbone of Formula 1, wherein at least two adjacent groups of $Z_1$, $Z_2$, $Z_{11}$ and $Z_{12}$ may be linked to form a saturated or unsaturated ring.

$Ar_{11}$, $Ar_{12}$ and $Ar_{13}$ are each independently selected from the group consisting of a substituted or unsubstituted $C_5$-$C_{60}$ aryl group, a substituted or unsubstituted $C_5$-$C_{50}$ aryloxy group, a substituted or unsubstituted $C_5$-$C_{50}$ arylthio group, and a substituted or unsubstituted. $C_4$-$C_{60}$ heteroaryl group.

$Ar_{11}$, $Ar_{12}$ and $Ar_{13}$ may be each independently selected from the group consisting of a substituted or unsubstituted $C_5$-$C_{20}$ aryl group and a substituted or unsubstituted $C_4$-$C_{20}$ heteroaryl group.

Examples of the substituted or unsubstituted $C_5$-$C_{20}$ arylene group and the substituted or unsubstituted $C_4$-$C_{20}$ heteroarylene group include, but are not limited to, a phenylene group, a $C_1$-$C_{10}$ alkylphenylene group, a $C_1$-$C_{10}$ alkoxyphenylene group, a halophenylene group, a cyanophenylene group, a dicyanophenylene group, a trifluoromethoxyphenylene group, an o-, m-, or p-tolylene group, an o-, m- or p-cumenylene group, a mesitylene group, a phenoxyphenylene group, a ($\alpha,\alpha$-dimethylbenzene)phenylene group, a ($C_1$-$C_{10}$alkylcyclohexyl)phenylene group, a (anthracenyl)phenylene group, a biphenylene group, a $C_1$-$C_{10}$ alkylbiphenylene group, a $C_1$-$C_{10}$ alkoxybiphenylene group, a pentalenyl group, an indenylene group, a naphthylene group, a $C_1$-$C_{10}$ alkylnaphthylene group, a $C_1$-$C_{10}$ alkoxynaphthylene group, a halonaphthylene group, a cyanonaphthylene group, a biphenyllenylene group, a $C_1$-$C_{10}$ alkyl biphenyllenylene group, a $C_1$-$C_{10}$ alkoxy biphenyllenylene group, a biphenylanthracenylene group, an anthracenylene group, an azulenylene group, a heptalenylene group, an acenaphthyllenylene group, a phenalenylene group, a fluorenylene group, an anthraquinolylene group, a methylanthrylene group, a phenanthrenylene group, a triphenyllenylene group, a pyrenylene group, a chrysenylene group, an ethylchrysenylene group, a picenylene group, a perylenylene group, a chloroperylenylene group, a pentaphenylene group, a pentacenylene group, a tetraphenyllenylene group, a hexaphenylene group, a hexacenylene group, a rubicenylene group, a coronenylene group, a trinaphthyllenylene group, a heptaphenylene group, a heptacenylene group, a pyranthrenylene group, an ovalenylene group, a carbazolylene group, a $C_1$-$C_{10}$ alkyl carbazolylene group, a thiophenylene group, an indolylene group, a purinylene group, a benzimidazolylene group, a quinolinylene group, a benzothiophenylene group, a parathiazinylene group, a pyrrolylene group, a pyrazolylene group, an imidazolylene group, an imidazolinylene group, an oxazolylene group, a thiazolylene group, a triazolylene group, a tetrazolylene group, an oxadiazolyl group, a pyridinylene group, a pyridazinylene group, a pyrimidinylene group, a pyrazinylene group, a thianthrenylene group, a pyrrolidinylene group, a pyrazolidinylene group, an imidazolidinylene group, a piperidinylene group, a piperazinylene group, and a morpholinylene group.

For example, $Ar_{11}$, $Ar_{12}$ and $Ar_{13}$ may be each independently selected from the group consisting of a phenyl group, a $C_1$-$C_{10}$ alkyl phenyl group, a di($C_1$-$C_{10}$ alkyl)phenyl group, a $C_6$-$C_{14}$ aryl phenyl group, a di($C_6$-$C_{14}$ aryl)phenyl group, a naphthyl group, a $C_1$-$C_{10}$ alkyl naphthyl group, a di($C_1$-$C_{10}$ alkyl)naphthyl group, a $C_6$-$C_{14}$ aryl naphthyl group, a di($C_6$-$C_{14}$ aryl)naphthyl group, an anthryl group, a $C_1$-$C_{10}$ alkyl anthryl group, a di($C_1$-$C_{10}$ alkyl)anthryl group, a $C_6$-$C_{14}$ aryl anthryl group, a di($C_6$-$C_{14}$ aryl)anthryl group, a phenanthryl group, a $C_1$-$C_{10}$ alkyl phenanthryl group, a di($C_1$-$C_{10}$ alkyl)phenanthryl group, a $C_6$-$C_{14}$ aryl phenanthryl group, a di($C_6$-$C_{14}$ aryl)phenanthryl group, a fluorenyl group, a $C_1$-$C_{10}$ alkyl fluorenyl group, a di($C_1$-$C_{10}$ alkyl)fluorenyl group, a $C_6$-$C_{14}$ aryl fluorenyl group, a di($C_6$-$C_{14}$ aryl) fluorenyl group, a pyridyl group, a $C_1$-$C_{10}$ alkyl pyridyl group, a di($C_1$-$C_{10}$ alkyl)pyridyl group, a pyrenyl group, a $C_1$-$C_{10}$ alkyl pyrenyl group, a di($C_1$-$C_{10}$ alkyl)pyrenyl group, a $C_6$-$C_{14}$ aryl pyrenyl group, a di($C_6$-$C_{14}$ aryl)pyrenyl group, a phenanthrolinyl group, a $C_1$-$C_{10}$ alkyl phenanthrolinyl group, a di($C_1$-$C_{10}$ alkyl)phenanthrolinyl group, a $C_6$-$C_{14}$ aryl phenanthrolinyl group, a di($C_6$-$C_{14}$ aryl)phenanthrolinyl group, a quinolinyl group, a $C_1$-$C_{10}$ alkyl quinolinyl group, a di($C_1$-$C_{10}$ alkyl)quinolinyl group, a $C_6$-$C_{14}$ aryl quinolinyl group, a di($C_6$-$C_{14}$ aryl)quinolinyl group, a benzoxazolyl group, a $C_1$-$C_{10}$ alkyl benzoxazolyl group, a di($C_1$-$C_{10}$ alkyl)benzoxazolyl group, a $C_6$-$C_{14}$ aryl benzoxazolyl group, a di($C_6$-$C_{14}$ aryl)benzoxazolyl group, a benzothiazolyl group, a $C_1$-$C_{10}$ alkyl benzothiazolyl group, a di($C_1$-$C_{10}$ alkyl)benzothiazolyl group, a $C_6$-$C_{14}$ aryl benzothiazolyl group, a di($C_6$-$C_{14}$ aryl)benzothiazolyl group, a benzimidazolyl group, a $C_1$-$C_{10}$ alkyl benzimidazolyl group, a di($C_1$-$C_{10}$ alkyl)benzimidazolyl group, a $C_6$-$C_{14}$ aryl benzimidazolyl group, a di($C_6$-$C_{14}$ aryl) benzimidazolyl group, an imidazolpyridinyl group, a $C_1$-$C_{10}$ alkyl imidazolpyridinyl group, a di($C_1$-$C_{10}$ alkyl) imidazolpyridinyl group, a $C_6$-$C_{14}$ aryl imidazolpyridinyl group, a di($C_6$-$C_{14}$ aryl)imidazolpyridinyl group, an imidazolpyrimidinyl group, a $C_1$-$C_{10}$ alkyl imidazolpyrimidinyl group, a di($C_1$-$C_{10}$ alkyl)imidazolpyrimidinyl group, a $C_6$-$C_{14}$ aryl imidazolpyrimidinyl group, a di($C_6$-$C_{14}$ aryl)imidazolpyrimidinyl group, a carbazolyl group, a $C_1$-$C_{10}$ alkyl carbazolyl group, a di($C_1$-$C_{10}$ alkyl)carbazolyl group, a $C_6$-$C_{14}$ aryl carbazolyl group, and a di($C_6$-$C_{14}$ aryl)carbazolyl group.

For example, $Ar_{11}$, $Ar_{12}$, and $Ar_{13}$ may be each independently selected from the group consisting of compounds represented by Formulae 3A through 3O below, but are not limited thereto:

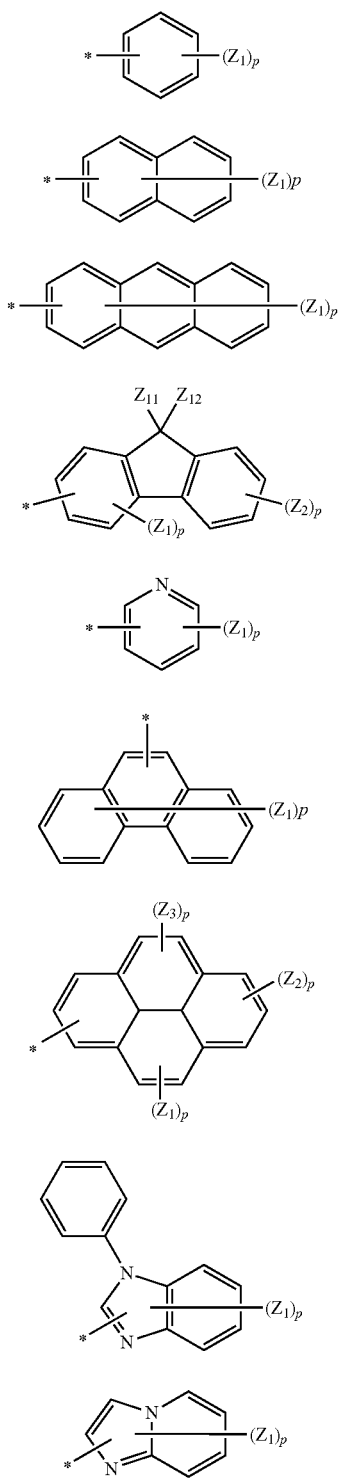

Formula 3A

Formula 3B

Formula 3C

Formula 3D

Formula 3E

Formula 3F

Formula 3G

Formula 3H

Formula 3I

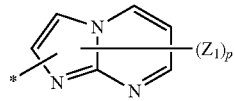

Formula 3J

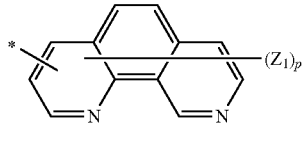

Formula 3K

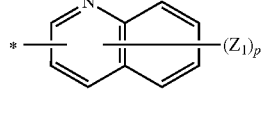

Formula 3L

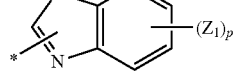

Formula 3M

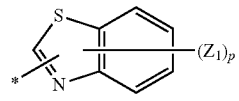

Formula 3N

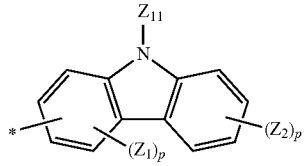

Formula 3O

In the formulae above, $Z_1$, $Z_2$, $Z_3$, $Z_{11}$ and $Z_{12}$ are each independently selected from the group consisting of a hydrogen atom, a deuterium atom, a $C_1$-$C_{10}$ alkyl group (for example, methyl, ethyl, propyl, isobutyl, sec-butyl or the like), a $C_1$-$C_{10}$ alkoxy group (for example, methoxy, ethoxy, propoxy, isopropyloxy, butoxy or the like), and a $C_6$-$C_{14}$ aryl group (for example, phenyl, naphthyl or the like); p is an integer from 1 to 8; and * denotes a binding site with $Ar_{11}$, $Ar_{12}$ or $Ar_{13}$, wherein at least two adjacent groups of $Z_1$, $Z_2$, $Z_3$, $Z_{11}$ and $Z_{12}$ may be linked to form a saturated or unsaturated ring.

a, b and b may be each independently an integer from 0 to 10.

For example, a, b, and c may be each independently 0, 1, 2 or 3.

"a" groups of —$Ar_1$— in —$(Ar_1)_a$—$(Ar_{11})$ may be identical to or different from each other, "b" groups of —$Ar_2$— in —N[—$(Ar_2)_b$—$(Ar_{12})$][—$(Ar_3)_c$—$(Ar_{13})$] may be identical to or different from each other, and "c" groups of —$Ar_3$— may be identical to or different from each other.

When one of $R_1$ through $R_{13}$ is selected from among the groups represented by —$(Ar_1)_a$—$(Ar_{11})$ and a=0, the substituent group may be represented by —$(Ar_{11})$. When one of $R_1$ through $R_{13}$ is selected from among the groups represented by —N[—$(Ar_2)_b$—$(Ar_{12})$][—$(Ar_3)_c$—$(Ar_{13})$], b≠0, and c=0, the substituent group may be represented by —N[—$(Ar_2)_b$—$(Ar_{12})$][—$(Ar_{13})$]. In this regard, $Ar_1$, $Ar_2$, $Ar_3$, $Ar_{11}$, $Ar_{12}$, $Ar_{13}$, a, b and c may be defined as described above.

In Formula 1 of the heterocyclic compound, $R_1$ through $R_{13}$ may be each independently selected from the group consisting of a hydrogen atom, a deuterium atom, a halogen atom, a cyano group, an amino group, a nitro group, a hydroxy group, a substituted or unsubstituted $C_1$-$C_{50}$ alkyl group, a group represented by —$(Ar_1)_a$—$(Ar_{11})$, and a group represented by —N[—$(Ar_2)_b$—$(Ar_{12})$][—$(Ar_3)_c$—$(Ar_{13})$];

Ar₁ through Ar₃ may be each independently selected from the group consisting of a substituted or unsubstituted $C_5$-$C_{20}$ arylene group and a substituted or unsubstituted $C_4$-$C_{20}$ heteroarylene group; $Ar_{11}$, $Ar_{12}$ and $Ar_{13}$ may be each independently selected from the group consisting of a phenyl group, a $C_1$-$C_{10}$ alkyl phenyl group, a di($C_1$-$C_{10}$ alkyl)phenyl group, a $C_6$-$C_{14}$ aryl phenyl group, a di($C_6$-$C_{14}$ aryl)phenyl group, a naphthyl group, a $C_1$-$C_{10}$ alkyl naphthyl group, a di($C_1$-$C_{10}$ alkyl)naphthyl group, a $C_6$-$C_{14}$ aryl naphthyl group, a di($C_6$-$C_{14}$ aryl)naphthyl group, an anthryl group, a $C_1$-$C_{10}$ alkyl anthryl group, a di($C_1$-$C_{10}$ alkyl)anthryl group, a $C_6$-$C_{14}$ aryl anthryl group, a di($C_6$-$C_{14}$ aryl)anthryl group, a phenanthryl group, a $C_1$-$C_{10}$ alkyl phenanthryl group, a di($C_1$-$C_{10}$ alkyl)phenanthryl group, a $C_6$-$C_{14}$ aryl phenanthryl group, a di($C_6$-$C_{14}$ aryl)phenanthryl group, a fluorenyl group, a $C_1$-$C_{10}$ alkyl fluorenyl group, a di($C_1$-$C_{10}$ alkyl)fluorenyl group, a $C_6$-$C_{14}$ aryl fluorenyl group, a di($C_6$-$C_{14}$ aryl)fluorenyl group, a pyridyl group, a $C_1$-$C_{10}$ alkyl pyridyl group, a di($C_1$-$C_{10}$ alkyl)pyridyl group, a pyrenyl group, a $C_1$-$C_{10}$ alkyl pyrenyl group, a di($C_1$-$C_{10}$ alkyl)pyrenyl group, a $C_6$-$C_{14}$ aryl pyrenyl group, a di($C_6$-$C_{14}$ aryl)pyrenyl group, a phenanthrolinyl group, a $C_1$-$C_{10}$ alkyl phenanthrolinyl group, a di($C_1$-$C_{10}$ alkyl)phenanthrolinyl group, a $C_6$-$C_{14}$ aryl phenanthrolinyl group, a di($C_6$-$C_{14}$ aryl)phenanthrolinyl group, a quinolinyl group, a $C_1$-$C_{10}$ alkyl quinolinyl group, a di($C_1$-$C_{10}$ alkyl) quinolinyl group, a $C_6$-$C_{14}$ aryl quinolinyl group, a di($C_6$-$C_{14}$ aryl)quinolinyl group, a benzoxazolyl group, a $C_1$-$C_{10}$ alkyl benzoxazolyl group, a di($C_1$-$C_{10}$ alkyl)benzoxazolyl group, a $C_6$-$C_{14}$ aryl benzoxazolyl group, a di($C_6$-$C_{14}$ aryl)benzoxazolyl group, a benzothiazolyl group, a $C_1$-$C_{10}$ alkyl benzothiazolyl group, a di($C_1$-$C_{10}$ alkyl)benzothiazolyl group, a $C_6$-$C_{14}$ aryl benzothiazolyl group, a di($C_6$-$C_{14}$ aryl)benzothiazolyl group, a benzimidazolyl group, a $C_1$-$C_{10}$ alkyl benzimidazolyl group, a di($C_1$-$C_{10}$ alkyl)benzimidazolyl group, a $C_6$-$C_{14}$ aryl benzimidazolyl group, a di($C_6$-$C_{14}$ aryl) benzimidazolyl group, an imidazolpyridinyl group, a $C_1$-$C_{10}$ alkyl imidazolpyridinyl group, a di($C_1$-$C_{10}$ alkyl)imidazolpyridinyl group, a $C_6$-$C_{14}$ aryl imidazolpyridinyl group, a di($C_6$-$C_{14}$ aryl)imidazolpyridinyl group, an imidazolpyrimidinyl group, a $C_1$-$C_{10}$ alkyl imidazolpyrimidinyl group, a di($C_1$-$C_{10}$ alkyl)imidazolpyrimidinyl group, a $C_6$-$C_{14}$ aryl imidazolpyrimidinyl group, a di($C_6$-$C_{14}$ aryl)imidazolpyrimidinyl group, a carbazolyl group, a $C_1$-$C_{10}$ alkyl carbazolyl group, a di($C_1$-$C_{10}$ alkyl)carbazolyl group, a $C_6$-$C_{14}$ aryl carbazolyl group, and a di($C_6$-$C_{14}$ aryl) carbazolyl group; and a, b and c may be independently an integer of 0, 1, 2, or 3.

The heterocyclic compound may be represented by Formula 2 below; i.e., a compound of Formula 1 wherein $R_4$, $R_5$, $R_6$, $R_7$, $R_9$, $R_{10}$, $R_{11}$, $R_{12}$ and $R_{13}$ are hydrogen atoms:

Formula 2

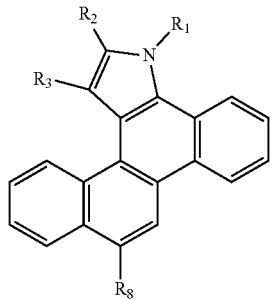

In Formula 2 above, $R_1$, $R_2$, $R_3$ and $R_4$ are each independently selected from the group consisting of a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_3$-$C_{50}$ cycloalkyl group, a substituted or unsubstituted $C_1$-$C_{50}$ alkoxy group, a group represented by —$(Ar_1)_a$—$(Ar_{11})$, and a group represented by —$N[$—$(Ar_2)_b$—$(Ar_{12})][$—$(Ar_3)_c$—$(Ar_{13})]$, wherein at least two adjacent groups of $R_1$ through $R_3$ may be linked to form a saturated or unsaturated ring.

$Ar_1$, $Ar_2$, $Ar_3$, $Ar_{11}$, $Ar_{12}$, $Ar_{13}$, a, b and c are described as above in conjunction with Formula 1.

When one of $R_1$, $R_2$, $R_3$ and $R_8$ is selected from among the groups represented by —$(Ar_1)_a$—$(Ar_{11})$ and a=0, the substituent group may be represented by —$(Ar_{11})$. When one of $R_1$, $R_2$, $R_3$ and $R_8$ is selected from among the groups represented by —$N[$—$(Ar_2)_b$—$(Ar_{12})][$—$(Ar_3)_c$—$(Ar_{13})]$, b≠0, and c=0, the substituent group may be represented by —$N[$—$(Ar_2)_b$—$(Ar_{12})][$—$(Ar_{13})]$.

For example, in Formula 2 of the heterocyclic compound, $R_1$ and $R_8$ may be each independently selected from the group consisting of a group represented by —$(Ar_1)_a$—$(Ar_{11})$ and a group represented by —$N[$—$(Ar_2)_b$—$(Ar_{12})][$—$(Ar_3)_c$—$(Ar_{13})]$; $R_2$ and $R_3$ may be each independently selected from the group consisting of a methyl group and a phenyl group; $Ar_1$ through $Ar_3$ may be each independently selected from the group consisting of a substituted or unsubstituted $C_5$-$C_{20}$ arylene group and a substituted or unsubstituted $C_4$-$C_{20}$ heteroarylene group; $Ar_{11}$, $Ar_{12}$ and $Ar_{13}$ may be each independently selected from the group consisting of a phenyl group, a $C_1$-$C_{10}$ alkyl phenyl group, a di($C_1$-$C_{10}$ alkyl)phenyl group, a $C_6$-$C_{14}$ aryl phenyl group, a di($C_6$-$C_{14}$ aryl)phenyl group, a naphthyl group, a $C_1$-$C_{10}$ alkyl naphthyl group, a di($C_1$-$C_{10}$ alkyl)naphthyl group, a $C_6$-$C_{14}$ aryl naphthyl group, a di($C_6$-$C_{14}$ aryl)naphthyl group, an anthryl group, a $C_1$-$C_{10}$ alkyl anthryl group, a di($C_1$-$C_{10}$ alkyl)anthryl group, a $C_6$-$C_{14}$ aryl anthryl group, a di($C_6$-$C_{14}$ aryl)anthryl group, a phenanthryl group, a $C_1$-$C_{10}$ alkyl phenanthryl group, a di($C_1$-$C_{10}$ alkyl) phenanthryl group, a $C_6$-$C_{14}$ aryl phenanthryl group, a di($C_6$-$C_{14}$ aryl)phenanthryl group, a fluorenyl group, a $C_1$-$C_{10}$ alkyl fluorenyl group, a di($C_1$-$C_{10}$ alkyl)fluorenyl group, a $C_6$-$C_{14}$ aryl fluorenyl group, a di($C_6$-$C_{14}$ aryl)fluorenyl group, a pyridyl group, a $C_1$-$C_{10}$ alkyl pyridyl group, a di($C_1$-$C_{10}$ alkyl)pyridyl group, a pyrenyl group, a $C_1$-$C_{10}$ alkyl pyrenyl group, a di($C_1$-$C_{10}$ alkyl)pyrenyl group, a $C_6$-$C_{14}$ aryl pyrenyl group, a di($C_6$-$C_{14}$ aryl)pyrenyl group, a phenanthrolinyl group, a $C_1$-$C_{10}$ alkyl phenanthrolinyl group, a di($C_1$-$C_{10}$ alkyl)phenanthrolinyl group, a $C_6$-$C_{14}$ aryl phenanthrolinyl group, a di($C_6$-$C_{14}$ aryl)phenanthrolinyl group, a quinolinyl group, a $C_1$-$C_{10}$ alkyl quinolinyl group, a di($C_1$-$C_{10}$ alkyl) quinolinyl group, a $C_6$-$C_{14}$ aryl quinolinyl group, a di($C_6$-$C_{14}$ aryl)quinolinyl group, a benzoxazolyl group, a $C_1$-$C_{10}$ alkyl benzoxazolyl group, a di($C_1$-$C_{10}$ alkyl)benzoxazolyl group, a $C_6$-$C_{14}$ aryl benzoxazolyl group, a di($C_6$-$C_{14}$ aryl)benzoxazolyl group, a benzothiazolyl group, a $C_1$-$C_{10}$ alkyl benzothiazolyl group, a di($C_1$-$C_{10}$ alkyl)benzothiazolyl group, a $C_6$-$C_{14}$ aryl benzothiazolyl group, a di($C_6$-$C_{14}$ aryl)benzothiazolyl group, a benzimidazolyl group, a $C_1$-$C_{10}$ alkyl benzimidazolyl group, a di($C_1$-$C_{10}$ alkyl)benzimidazolyl group, a $C_6$-$C_{14}$ aryl benzimidazolyl group, a di($C_6$-$C_{14}$ aryl) benzimidazolyl group, an imidazolpyridinyl group, a $C_1$-$C_{10}$ alkyl imidazolpyridinyl group, a di($C_1$-$C_{10}$ alkyl)imidazolpyridinyl group, a $C_6$-$C_{14}$ aryl imidazolpyridinyl group, a di($C_6$-$C_{14}$ aryl)imidazolpyridinyl group, an imidazolpyrimidinyl group, a $C_1$-$C_{10}$ alkyl imidazolpyrimidinyl group, a di($C_1$-$C_{10}$ alkyl)imidazolpyrimidinyl group, a $C_6$-$C_{14}$ aryl imidazolpyrimidinyl group, a di($C_6$-$C_{14}$ aryl)imidazolpyrimidinyl group, a carbazolyl group, a $C_1$-$C_{10}$ alkyl carbazolyl group, a di($C_1$-$C_{10}$ alkyl)carbazolyl group, a $C_6$-$C_{14}$ aryl carbazolyl group, and a di($C_6$-$C_{14}$ aryl) carbazolyl group; and a, b and c may be independently an integer of 0, 1, 2 or 3.

Examples of the heterocyclic compound of Formula 1 include, but are not limited to, Compounds 1 through 60 represented below.

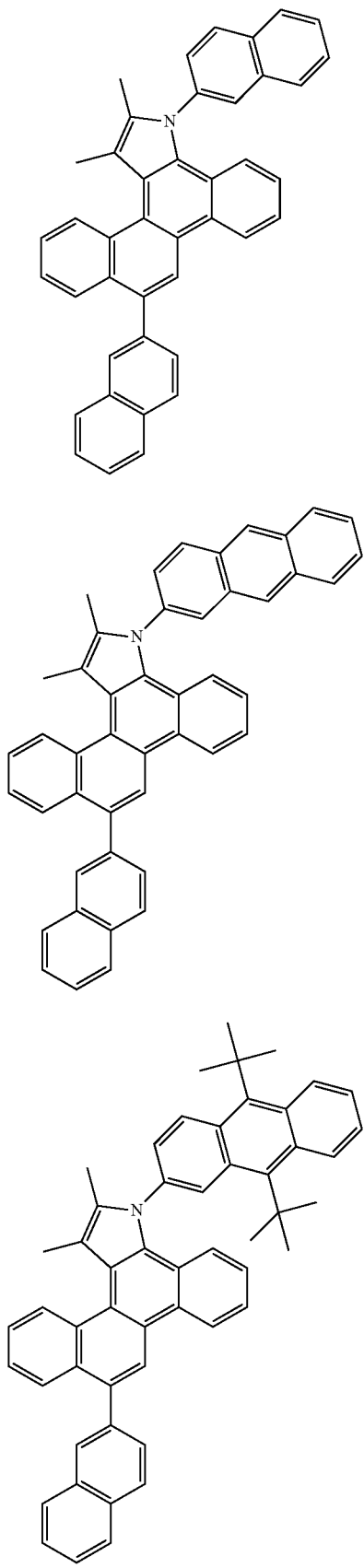
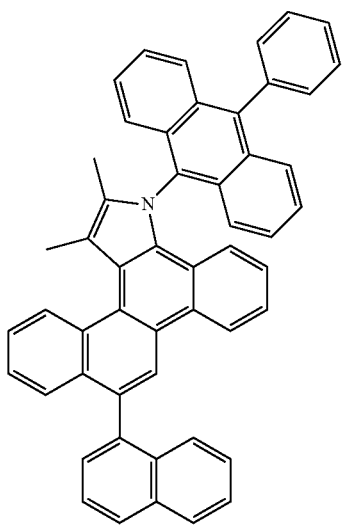
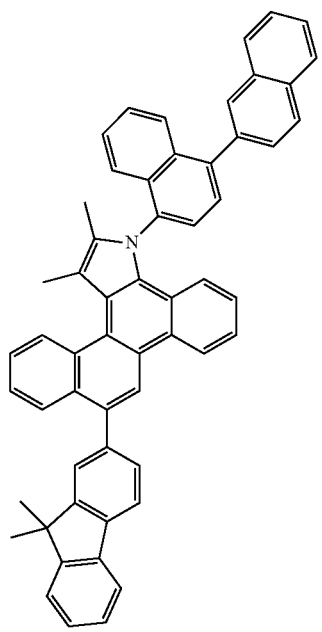

5
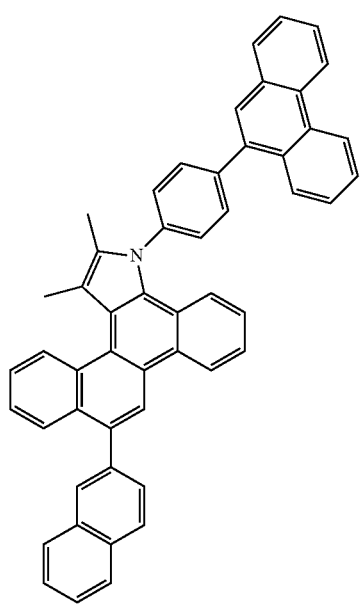
6
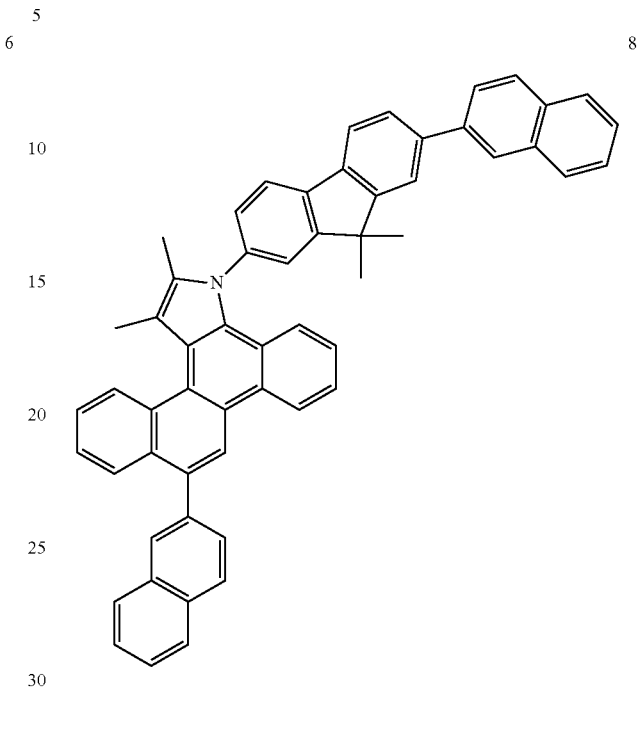
7
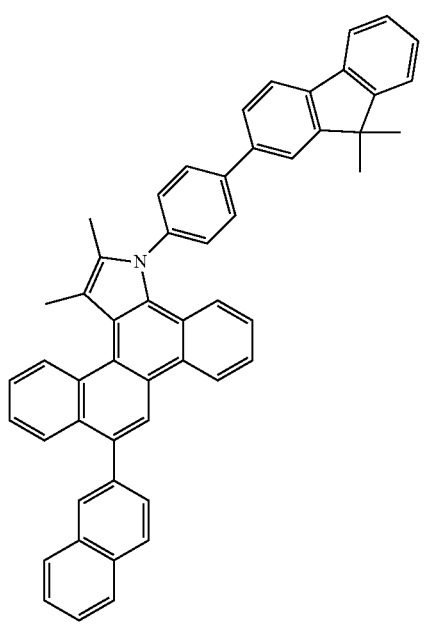
8
9
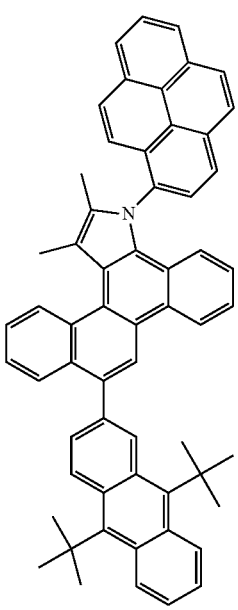

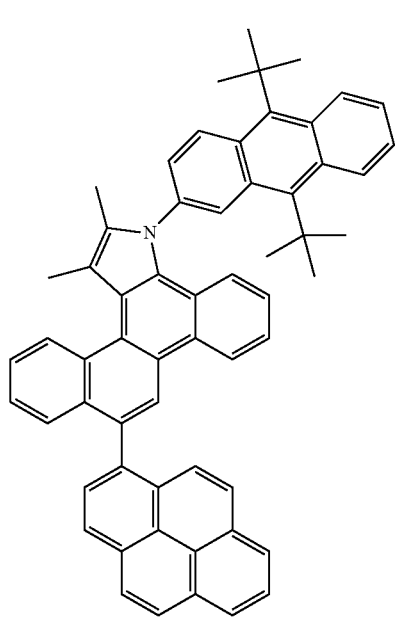
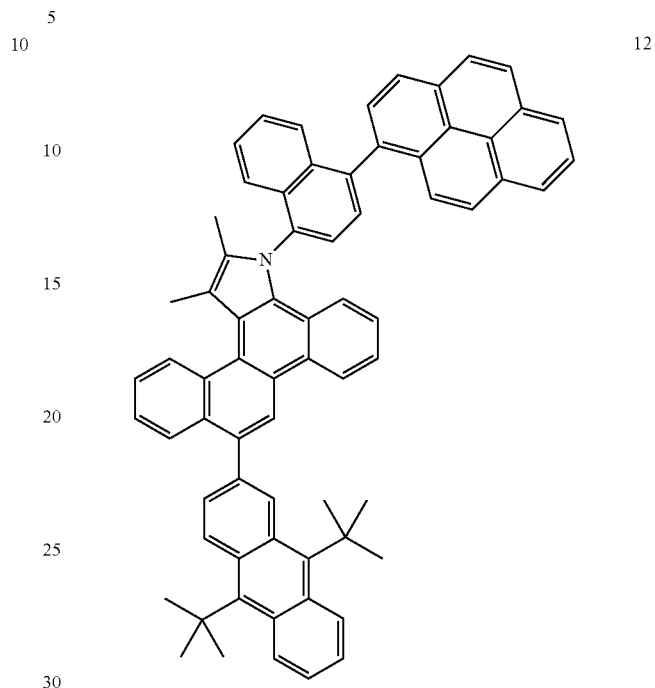
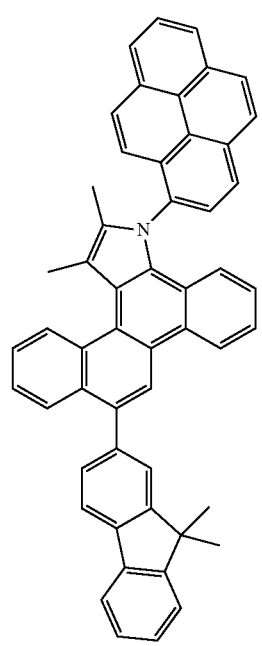
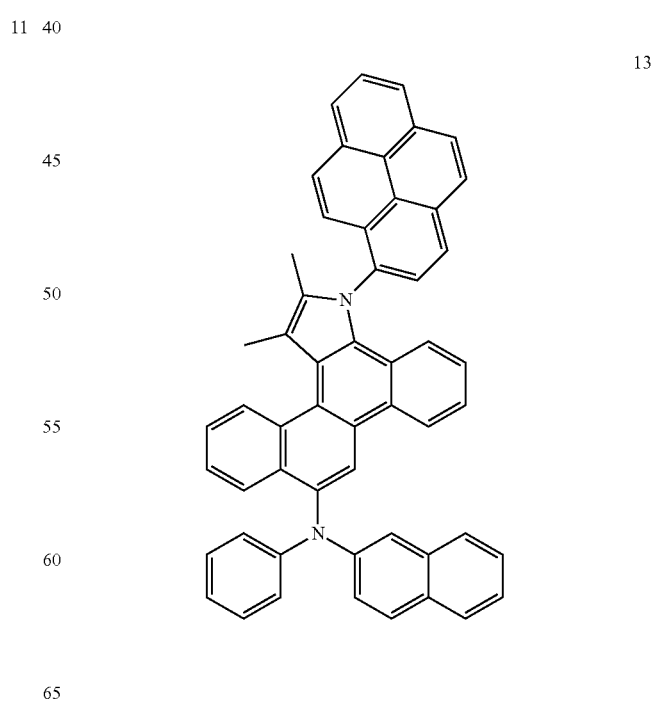

14
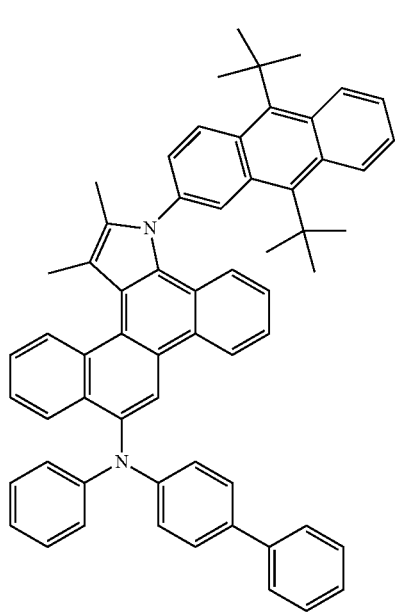
15
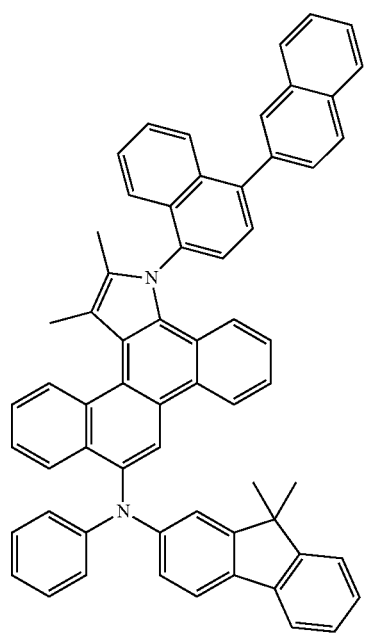
16
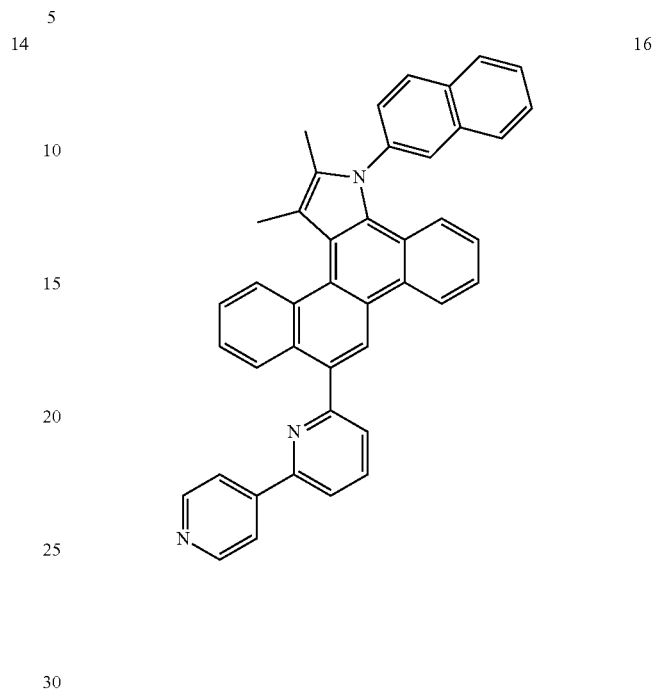
17
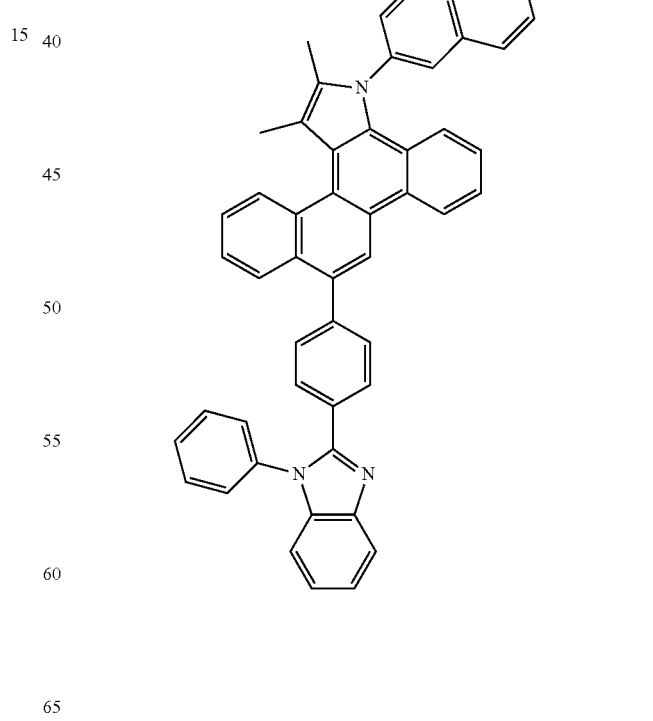

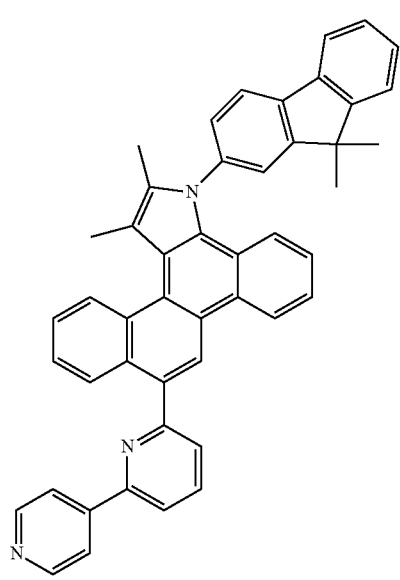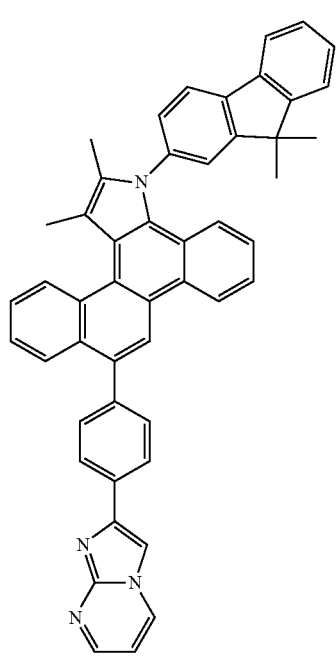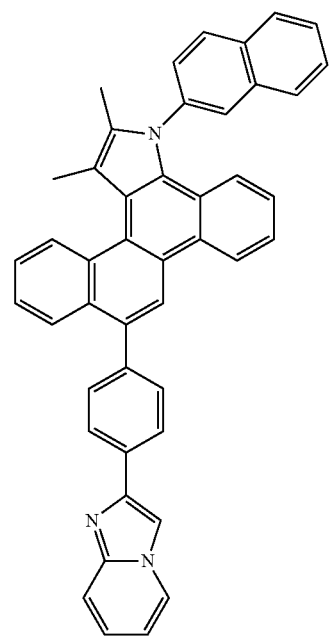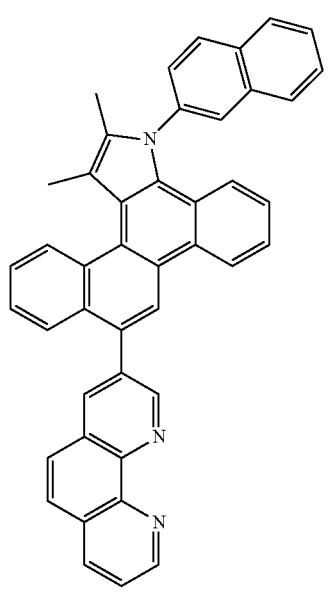

21
-continued
22
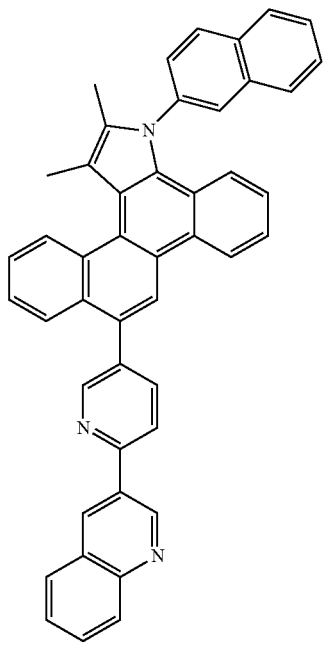
22
-continued
24
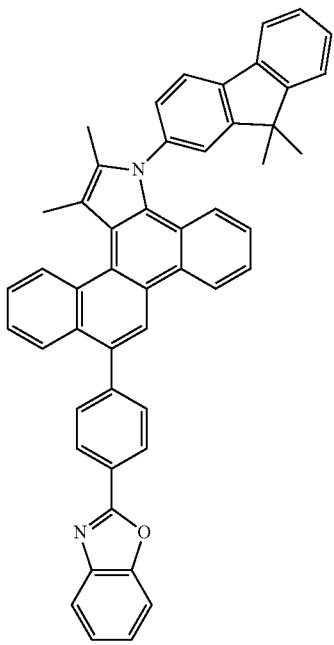
23
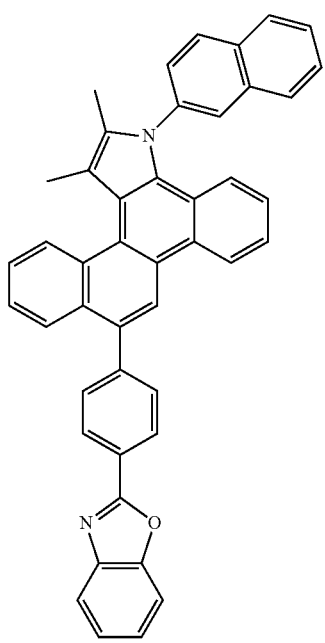
25
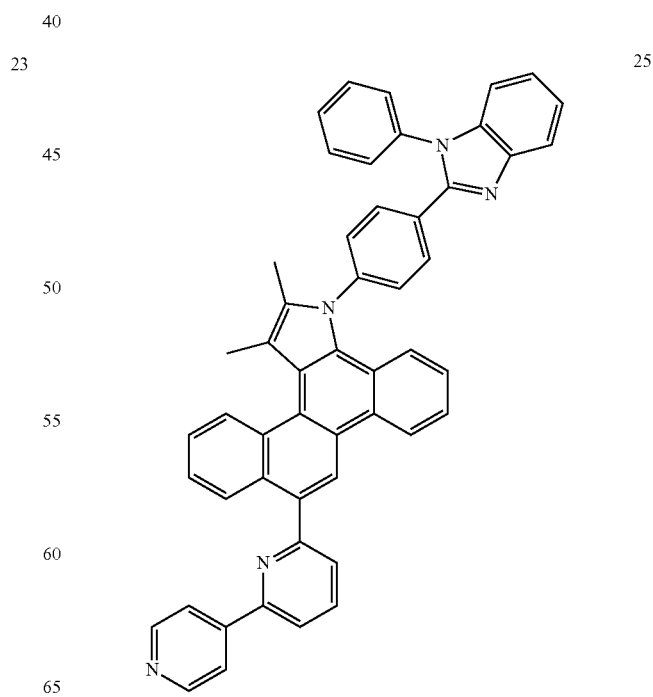

23
-continued
26
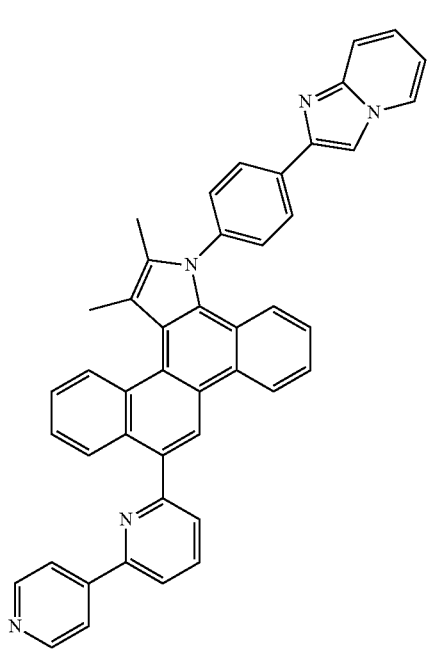
27
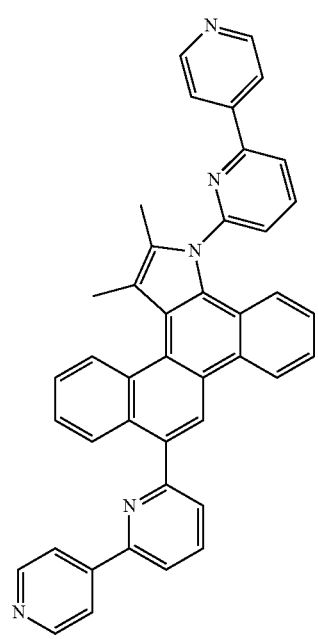
24
-continued
28
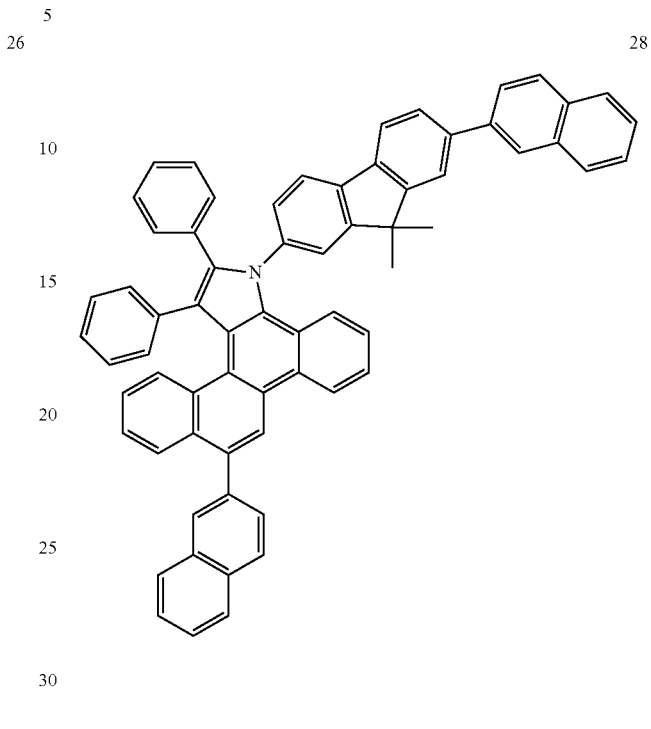
29
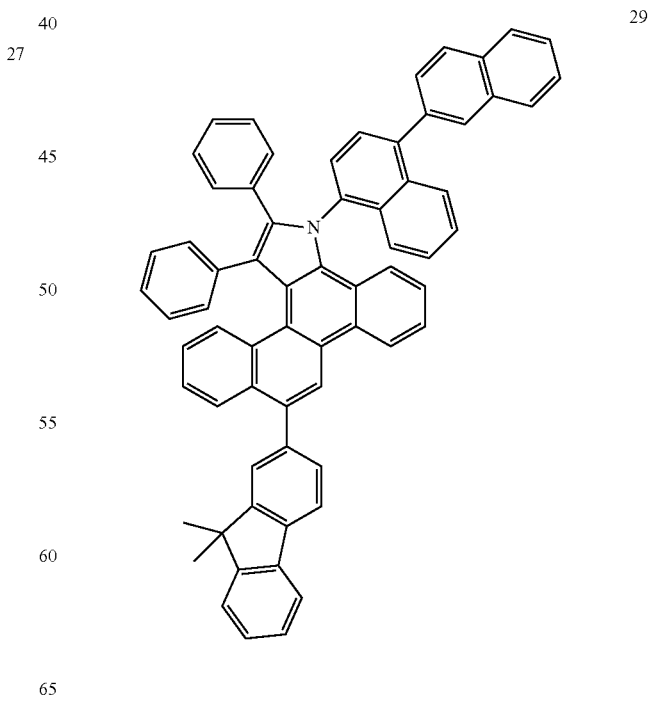

25
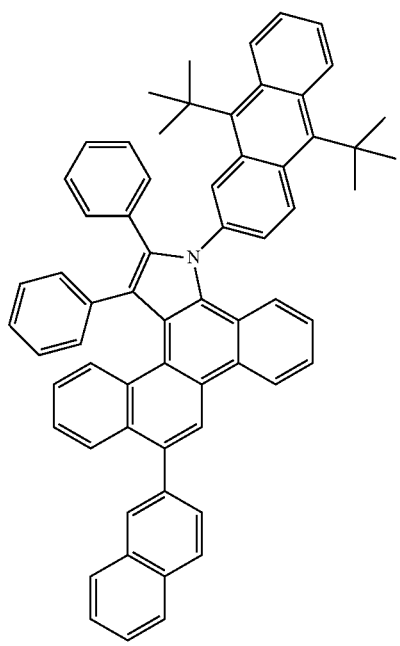
30
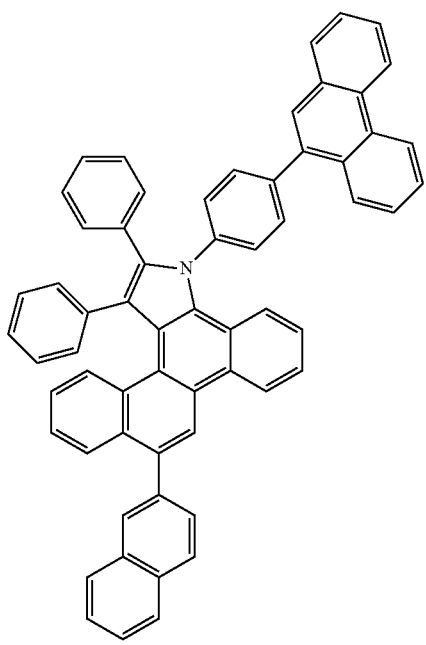
31
26
32
33
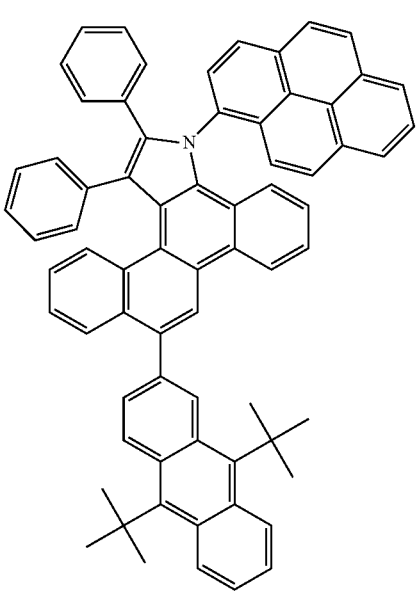

34
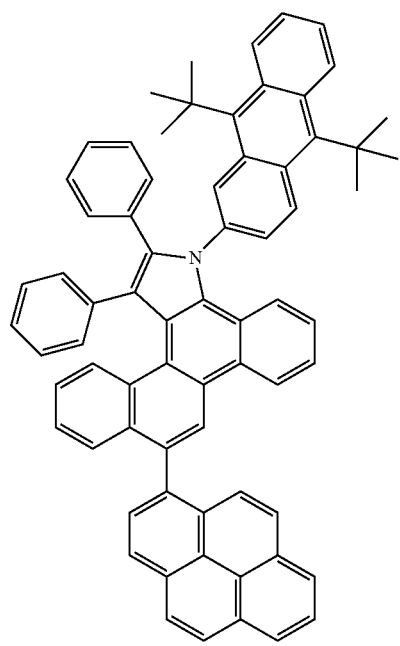
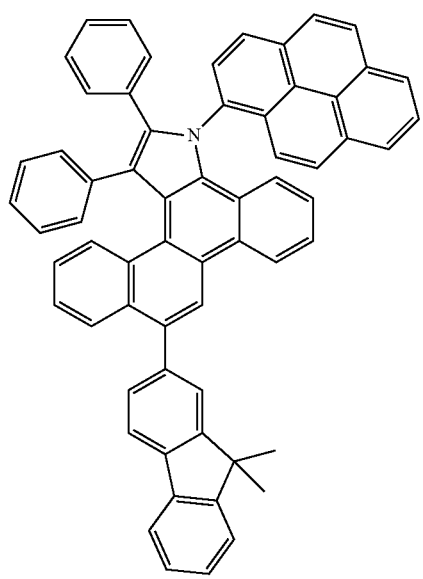
36
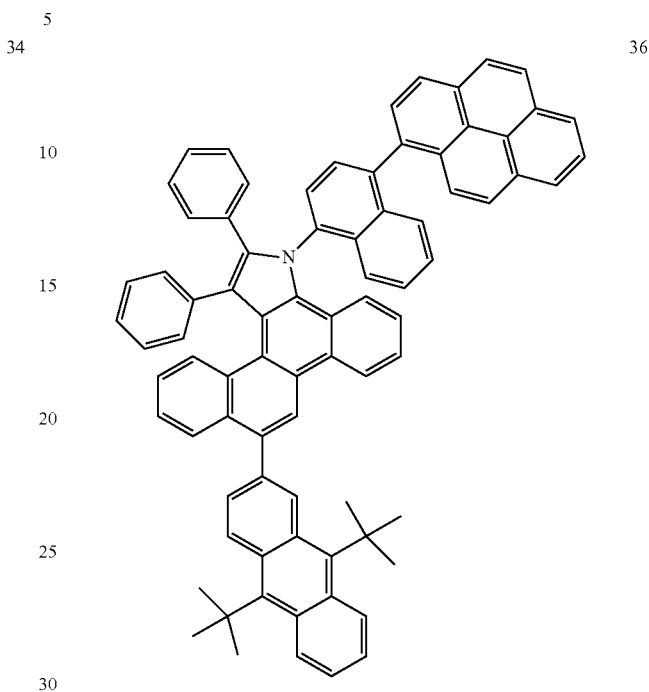
37
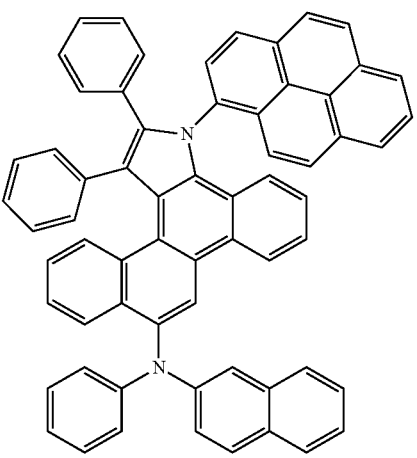

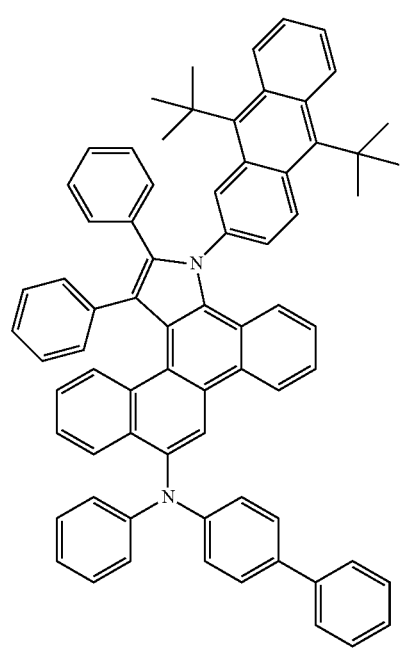
38
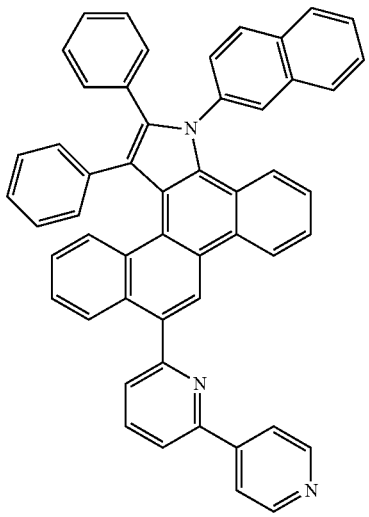
40
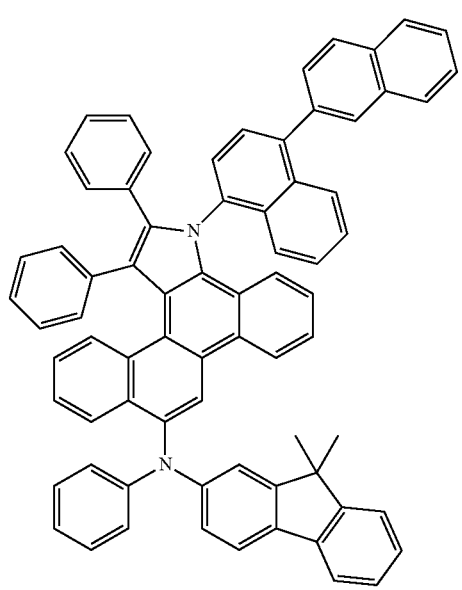
39
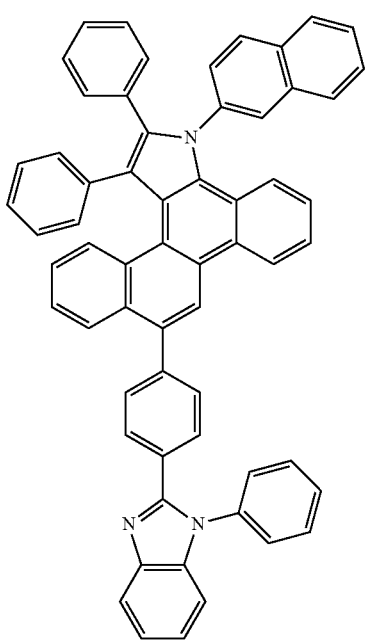
41

31
-continued
42
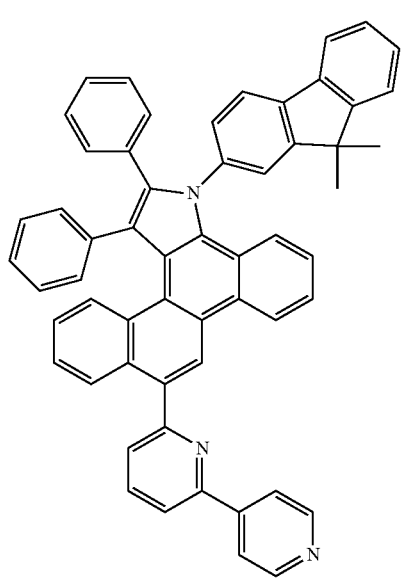
43
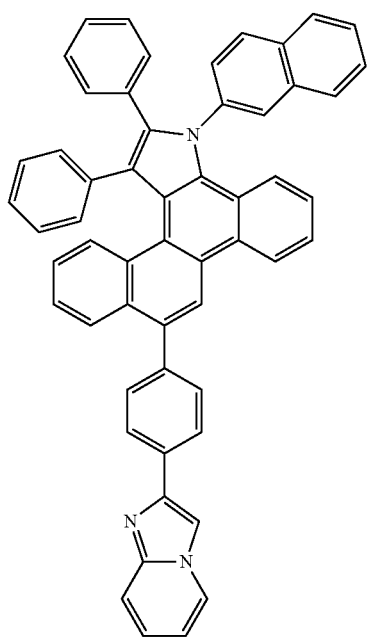
32
-continued
44
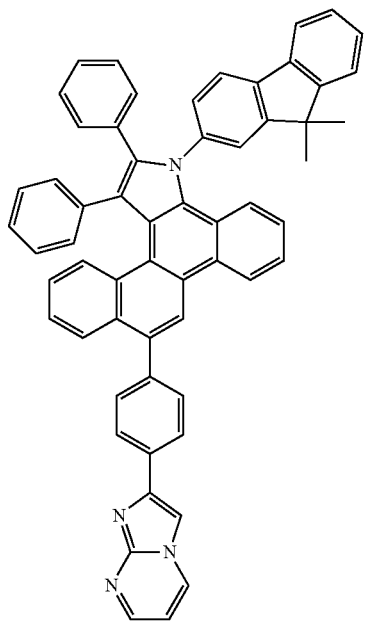
45
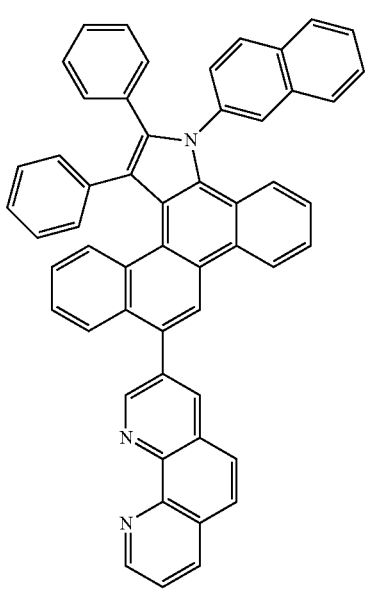

33
-continued
46
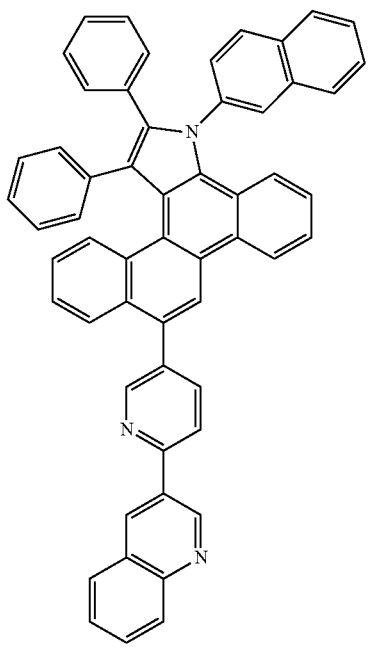
47
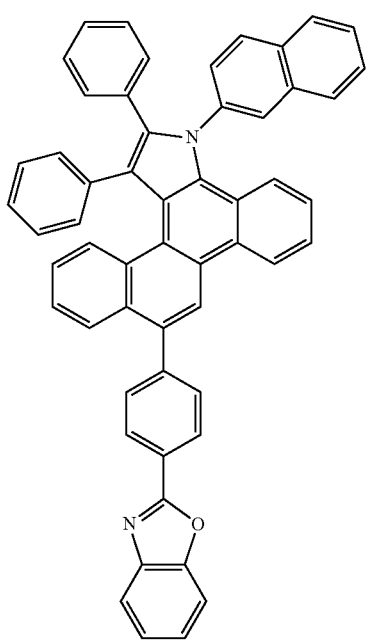
34
-continued
48
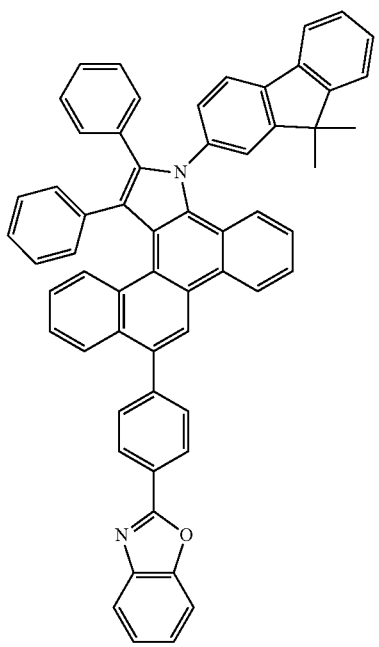
49
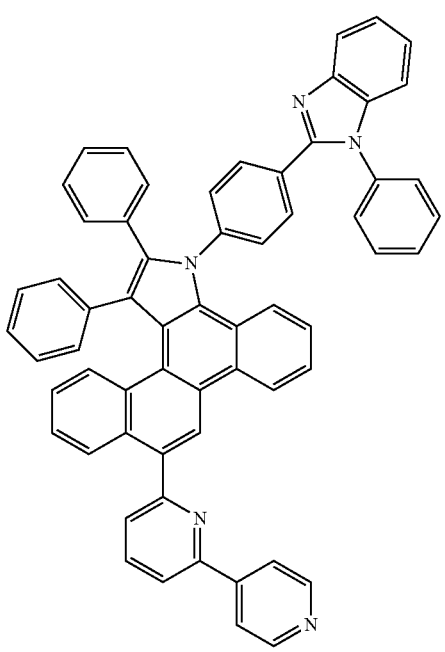

50
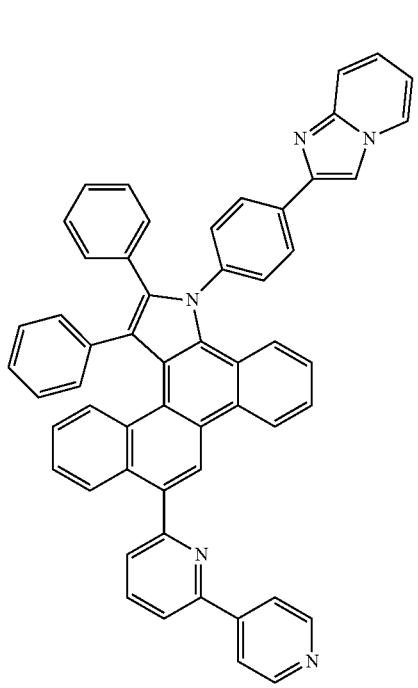
51
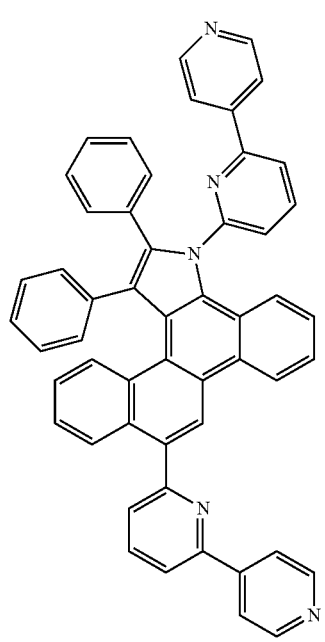
52
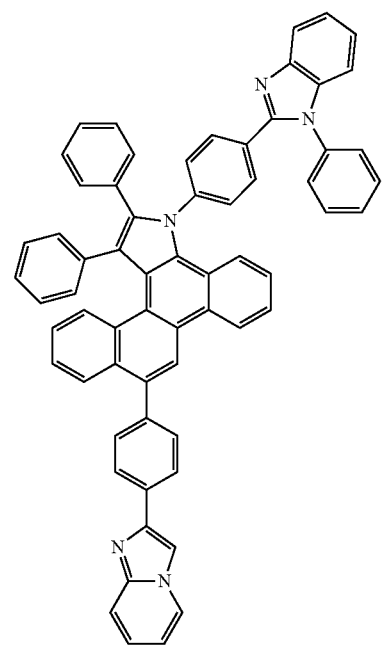
53
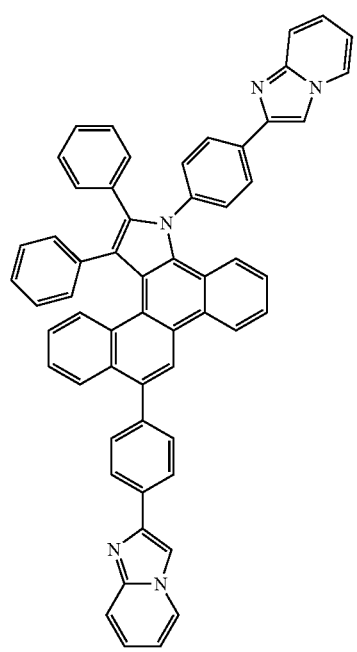

54
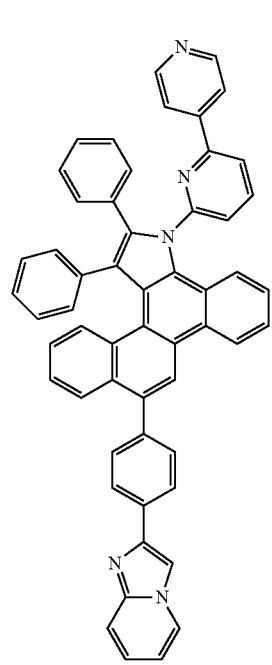
55
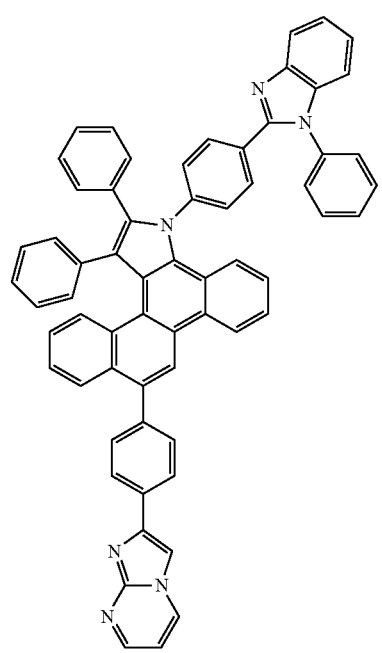
56
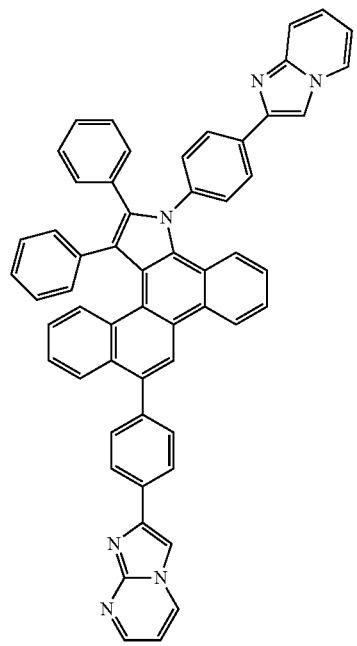
57
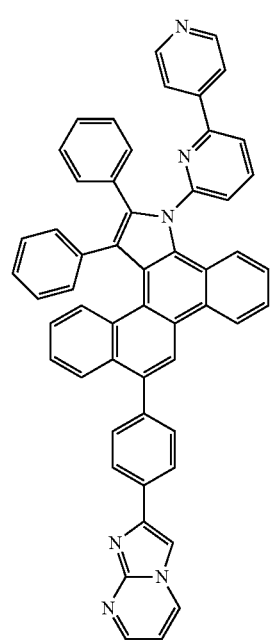

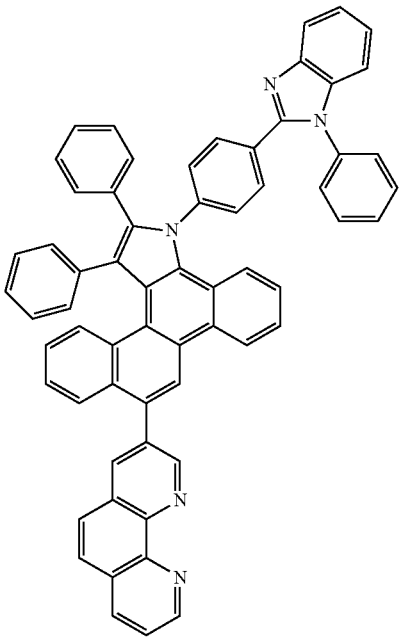

58

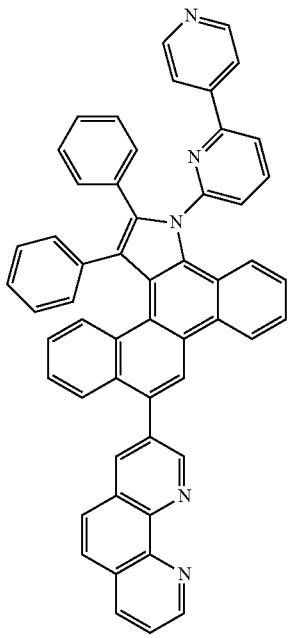

60

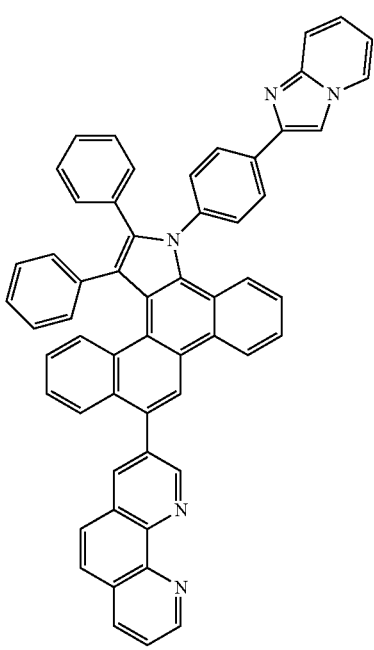

59

The $C_1$-$C_{50}$ alkyl group used herein may be a linear or branched group.

Examples of the $C_1$-$C_{50}$ alkyl group include, but are not limited to, methyl, ethyl, propyl, isobutyl, sec-butyl, pentyl, iso-amyl, hexyl, heptyl, octyl, nonanyl, and dodecyl. At least one hydrogen atom of the $C_1$-$C_{50}$ alkyl group may be substituted with a deuterium atom, a halogen atom, a cyano group, an amino group, an amidino group, a nitro group, a hydroxyl group, a hydrazinyl group, a hydrazonyl group, a carboxyl group or a salt thereof, a sulfonic acid group or a salt thereof, a phosphoric acid or a salt thereof, a $C_1$-$C_{30}$ alkyl group, a $C_1$-$C_{30}$ alkoxy group, a $C_2$-$C_{30}$ alkenyl group, a $C_2$-$C_{30}$ alkynyl group, a $C_6$-$C_{20}$ aryl group, a $C_4$-$C_{20}$ heteroaryl group, —N($Q_1$)($Q_2$), or —Si($Q_3$)($Q_4$)($Q_5$), wherein $Q_1$ through $Q_5$ may be each selected from the group consisting of a hydrogen atom, deuterium atom, a halogen atom, a cyano group, an amino group, an amidino group, a nitro group, a hydroxyl group, a hydrazinyl group, a hydrazonyl group, a carboxyl group or a salt thereof, a sulfonic acid group or a salt thereof, a phosphoric acid or a salt thereof, a $C_1$-$C_{30}$ alkyl group, a $C_1$-$C_{30}$ alkoxy group, a $C_2$-$C_{30}$ alkenyl group, a $C_2$-$C_{30}$ alkynyl group, a $C_6$-$C_{20}$ aryl group, or a $C_4$-$C_{20}$ heteroaryl group.

The unsubstituted $C_2$-$C_{50}$ alkenyl group indicates a hydrocarbon having at least one carbon-carbon double bond in the center or at a terminal of the unsubstituted $C_2$-$C_{50}$ alkyl group. Examples of the alkenyl group include an ethenyl group, a properlyl group, a butenyl group, and the like. At least one hydrogen atom in the unsubstituted $C_2$-$C_{50}$ alkenyl group may be substituted with the substituents described in conjunction with the substituted $C_1$-$C_{50}$ alkyl group.

The unsubstituted $C_2$-$C_{50}$ alkynyl group indicates a hydrocarbon having at least one carbon-carbon triple bond in the center or at a terminal of the $C_2$-$C_{50}$ alkyl group defined above. Examples of the unsubstituted $C_2$-$C_{20}$ alkynyl group include acetylene, propylene, phenylacetylene, naphthylacetylene, isopropylacetylene, t-butylacetylene, and diphenylacetylene. At least one hydrogen atom in the alkynyl group may be substituted with the substituents described above in conjunction with the $C_1$-$C_{50}$ alkyl group.

The unsubstituted $C_3$-$C_{50}$ cycloalkyl group used herein refers to a $C_3$-$C_{50}$ cyclic alkyl group wherein at least one hydrogen atom in the cycloalkyl group may be substituted with substituents described above in connection with the $C_1$-$C_{50}$ alkyl group.

The unsubstituted $C_1$-$C_{50}$ alkoxy group used herein is a group having a structure of —OA wherein A is an unsubstituted $C_1$-C50 alkyl group as described above. Examples thereof include a methoxy group, an ethoxy group, a propoxy group, an isopropyloxy group, a butoxy group, and a pentoxy group. At least one hydrogen atom of the alkoxy group may be substituted with the same substituent groups as described above in conjunction with the $C_1$-$C_{50}$ alkyl group.

The unsubstituted $C_5$-$C_{60}$ aryl group used herein refers to a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with the substituents described above in conjunction with the $C_1$-$C_{50}$ alkyl group. Examples of the substituted or unsubstituted $C_6$-$C_{30}$ aryl group include, but are not limited to, a phenyl group, a $C_1$-$C_{10}$ alkylphenyl group (for example, an ethylphenyl group), a halophenyl group (for example, an o-, m-, and p-fluorophenyl group, a dichlorophenyl group), a cyanophenyl group, dicyanophenyl group, a trifluoromethoxyphenyl group, a biphenyl group, a halobiphenyl group, a cyanobiphenyl group, a $C_1$-$C_{10}$ alkyl biphenyl group, a $C_1$-$C_{10}$ alkoxybiphenyl group, a o-, m-, and p-toryl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (for example, a fluoronaphthyl group), a $C_1$-$C_{10}$ alkylnaphthyl group (for example, a methylnaphthyl group), a $C_1$-$C_{10}$ alkoxynaphthyl group (for example, a methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted $C_5$-$C_{50}$ aryloxy group is a group represented by —OA1 wherein A1 is a $C_5$-$C_{30}$ aryl group. Examples of the aryloxy group may include a phenoxy group. At least one hydrogen atom in the aryloxy group may be substituted with the substituents described above in conjunction with the $C_1$-$C_{50}$ alkyl group.

The unsubstituted $C_5$-$C_{50}$ arylthio group is a group represented by —SA1 wherein A1 is a $C_5$-$C_{50}$ aryl group. Examples of the arylthio group include, but are not limited to, a phenylthio group, a naphthylthio group, and a fluorenylthio group. At least one hydrogen atom in the arylthio group may be substituted with the substituents described above in conjunction with the $C_1$-$C_{50}$ alkyl group.

The unsubstituted $C_4$-$C_{60}$ heteroaryl group used herein includes one, two or three hetero atoms selected from among N, O, P and S. At least two rings may be fused to each other or linked to each other by a single bond. Examples of the unsubstituted $C_4$-$C_{60}$ heteroaryl group may include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, and an isoquinolinyl group. At least one hydrogen atom in the heteroaryl group may be substituted with the substituents described above in conjunction with the $C_1$-$C_{50}$ alkyl group.

Throughout the specification a saturated ring or unsaturated ring formed by the linking of at least two adjacent substituents indicates a substituent including at least two rings formed by the fusing of at least one aromatic ring and/or at least one non-aromatic ring. Examples of this substituent include some of the substituents described above in conjunction with the aryl group or heteroaryl group.

An organic light-emitting device according to an embodiment of the present invention includes a first electrode, a second electrode disposed opposite to the first electrode, and an organic layer disposed between the first electrode and the second electrode, the organic layer including the heterocylic compound of Formula 1 described above.

The heterocyclic compound of Formula 1 may be suitable as a material for an emission layer, an electron transport layer or an electron injection layer of an organic light-emitting device. Due to the inclusion of the heterocyclic group in its molecular structure, the heterocyclic compound of Formula 1 may have a high glass transition temperature (Tg) or a high melting point, and may prevent crystallization. An organic light-emitting device manufactured using the heterocyclic compound of Formula 1, in which a chrysene group and an indole group are fused, has excellent durability when stored or operated. If further including a substituent, such as a fluorene group, the heterocyclic compound of Formula 1 may have a higher glass transition temperature (Tg) or a higher decomposition temperature (Td), and thus, the organic light-emitting device may have improved characteristics at high temperatures. Thus, when such a heterocyclic compound is used as an organic emission material, resistance to Joule's heat produced inside organic layers, between organic layers, or between an organic layer and a metal electrode may be increased, and resistance to a high-temperature environment may be increased.

The organic layer including the heterocyclic compound of Formula 1 may be an electron injection layer, an electron transport layer, an emission layer, or a single layer having both the abilities to inject and transport electrons.

For example, the organic layer including the heterocyclic compound of Formula 1 may be an emission layer. In this case, the heterocyclic compound of Formula 1 may be used as a fluorescent host, a phosphorescent host, or a fluorescent dopant.

In the organic light-emitting device according to the current embodiment of the present invention, when the emission layer, the electron injection layer or the electron transport layer includes the heterocyclic compound of Formula 1, the emission layer may include an anthracene compound, an arylamine compound or a styryl compound, which are widely known, wherein the anthracene compound, the arylamine compound or the styryl compound may be unsubstituted or substituted with a substituent described above in conjunction with the $C_1$-$C_{50}$ alkyl group.

In the organic light-emitting device according to the current embodiment of the present invention, when the electron injection layer or the electron transport layer includes the heterocyclic compound of Formula 1, a red emission layer, a green emission layer, a blue emission layer or a white emission layer may include a widely-known phosphorescent compound.

Meanwhile, the first electrode may be an anode, and the second electrode may be a cathode, but the reverse is also possible.

In the organic light-emitting described above, the organic layer may further include at least one layer selected from the group consisting of a hole injection layer, a hole transport layer, an electron blocking layer, an emission layer, a hole blocking layer, an electron transport layer and an electron injection layer, if required.

For example, the organic light-emitting device according to the current embodiment of the present invention may have a structure of first electrode/hole injection layer/emission layer/second electrode, a structure of first electrode/hole injection layer/hole transport layer/emission layer/electron transport layer/second electrode, or a structure of first electrode/hole injection layer/hole transport layer/emission layer/ electron transport layer/electron injection layer/second electrode. Alternatively, the organic light-emitting device may also have a first electrode/single layer having both hole injection and hole transport capabilities/EML/ETL/second electrode structure, or a first electrode/single layer having both hole injection and hole transport capabilities/EML/ETL/EIL/ second electrode structure.

The organic light emitting device according to the current embodiment of the present invention may be a top-emission organic light-emitting device or a bottom-emission organic light-emitting device.

Hereinafter, a method of manufacturing an OLED according to an embodiment of the present invention will be described with reference to FIG. 1. Referring to FIG. 1, the organic light-emitting device according to the present embodiment includes a substrate, a first electrode (anode), a hole injection layer (HIL), a hole transport layer (HTL), an emission layer (EML), an electron transport layer (ETL), an electron injection layer (EIL), and a second electrode (cathode).

First, the first electrode is formed by depositing a first electrode-forming material having a high work function on a substrate, by deposition or sputtering. The first electrode may constitute an anode or a cathode. The substrate may be any substrate that is used in conventional organic light emitting devices. In this regard, the substrate may be a glass or transparent plastic substrate with excellent mechanical strength, thermal stability, transparency, surface smoothness, ease of handling, and water resistance. Examples of the first electrode material include materials, such as indium tin oxide (ITO), indium zinc oxide (IZO), tin oxide (SnO2), zinc oxide (ZnO), aluminum (Al), silver (Ag), and magnesium (Mg), which have excellent conductivity. The first electrode may be formed as a transparent or reflective electrode.

Then, a HIL may be formed on the first electrode by vacuum deposition, spin coating, casting, Langmuir Blodgett (LB) deposition, or the like.

When the HIL is formed using vacuum deposition, the deposition conditions may vary according to a material that is used to form the HIL, and the structure and thermal characteristics of the HIL to be formed. For example, the deposition conditions may include a deposition temperature of 100 to 500° C., a vacuum pressure of $10^{-8}$ to $10^{-3}$ torr, and a deposition rate of 0.01 to 100 Å/sec.

When the HIL is formed using spin coating, coating conditions may vary according to a material that is used to form the HIL, and the desired structure and thermal properties of the HIL to be formed. For example, the coating speed may be in a range of about 2000 rpm to about 5000 rpm, and a temperature for heat treatment, which is performed to remove a solvent after coating, may be in a range of about 80° C., to about 200° C.

The HIL may be formed of any known materials used to form a HIL.

Examples of the HIL material include, but are not limited to, a phthalocyanine compound such as copper phthalocyanine, 4,4',4"-tris (3-methylphenylphenylamino) triphenylamine (m-MTDATA), N,N'-diphenyl-N,N'-bis(1-naphthyl)-1,1'-biphenyl-4,4"-diamine (NPB), TDATA, 2-TNATA, polyaniline/dodecylbenzenesulfonic acid (Pani/DBSA), poly (3,4-ethylenedioxythiophene)/poly(4-styrenesulfonate (PEDOT/PSS), polyaniline/camphor sulfonic acid (Pani/CSA), and (polyaniline)/poly(4-styrenesulfonate) (PANI/PSS).

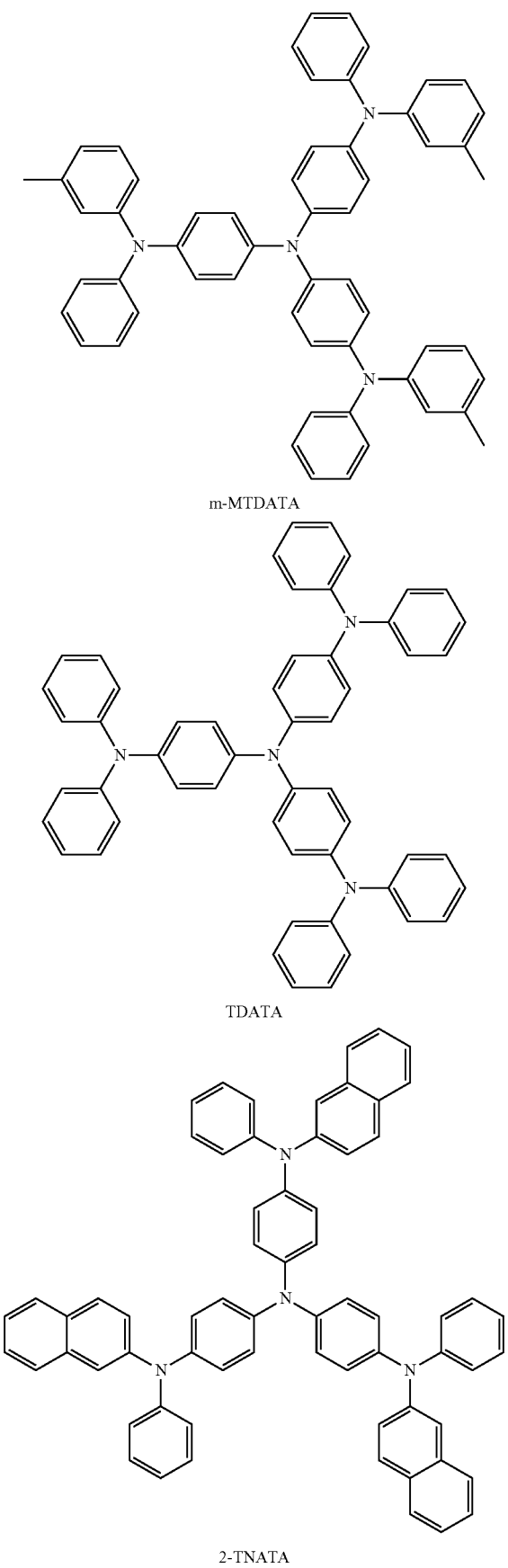

m-MTDATA

TDATA

2-TNATA

The thickness of the HIL may be in a range of about 100 to about 10,000 Å, for example, about 100 to about 1,000 Å. When the thickness of the HIL is within the above range, the HIL may have excellent hole injection characteristics without a substantial increase in driving voltage.

Then, a HTL may be formed on the HIL by vacuum deposition, spin coating, casting, Langmuir-Blodgett (LB) deposition, or the like. When the HTL is formed using vacuum deposition or spin coating, the deposition or coating conditions may be similar to those applied to form the HIL, though the deposition or coating conditions may vary according to the material that is used to form the HTL.

The HTL may be formed of any known materials used to form a HTL.

Examples of the HTL material include, but are not limited to, cabazol derivatives such as N-phenylcarbazol or polyvinylcarbazol, and amine derivatives having an aromatic condensed ring, such as N,N'-diphenyl-N,N'-bis(1-naphthyl)-1,1'-biphenyl-4,4"-diamine (NPB) and N,N'-bis(3-methylphenyl)-N,N'-diphenyl-[1,1-biphenyl]-4,4'-diamine (TPD). Among these materials. TCTA may not only transport holes but also inhibit excitons from being diffused from the EML.

The thickness of the HTL may be in a range of about 50 to 1,000 Å, for example, about 100 to about 2,500 Å. When the thickness of the HTL is within the above range, the HTL may have excellent hole transport characteristics without a substantial increase in driving voltage.

Then, an EML may be formed on the HTL by vacuum deposition, spin coating, casting, LB, or the like. When the EML is formed using vacuum deposition or spin coating, the deposition or coating conditions may be similar to those applied to form the HIL, though the deposition and coating conditions may vary according to the material that is used to form the EML.

The EML may include the heterocyclic compound of Formula 1 described above. For example, the heterocyclic compound of Formula 1 may be used as a host or a dopant. In addition to the heterocyclic compound of Formula 1, various known light-emitting materials, such as known hosts and dopants, may be used to form the EML. Dopants used to form the EML may include either a fluorescent dopant or a phosphorescent dopant, which are widely known in the art.

Examples of the host may include, but are not limited to, Alq3, 4,4'-N,N'-dicarbazole-biphenyl (CPB), 9,10-di(naphthalene-2-yl)anthracene (ADN), and distyrylarylene (DSA).

Examples of known dopants include, but are not limited to, PtOEP, $Ir(piq)_3$, $Btp_2Ir(acac)$, $Ir(ppy)_3$ (ppy=phenylpyridine), $Ir(ppy)_2(acac)$, $Ir(mpyp)_3$, C545T (10-(2-benzothiazolyl)-2,3,6,7-tetrahydro-1,1,7,7-tetramethyl-1H,5H,11H-(1)benzopyropyrano(6,7-8-i,j)quinolizine-11-on), $F_2Irpic$, $(F_2ppy)_2Ir(tmd)$, $Ir(dfppz)_3$, ter-fluorene, 4,4'-bis(4-diphenylaminostyryl)biphenyl (DPAVBi), and 2,5,8,11-tetra-t-butyl pherylene (TBP).

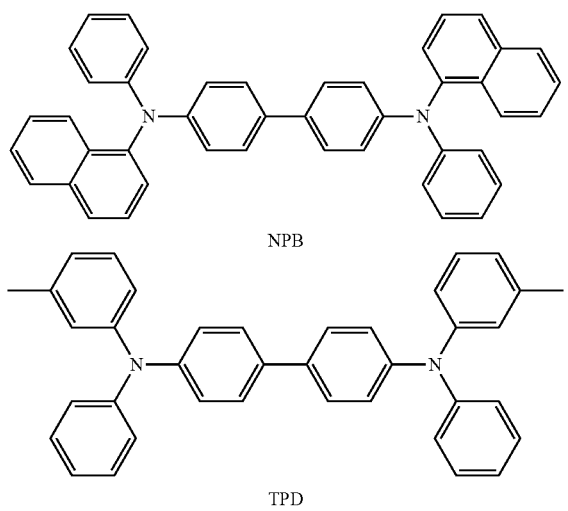

NPB

TPD

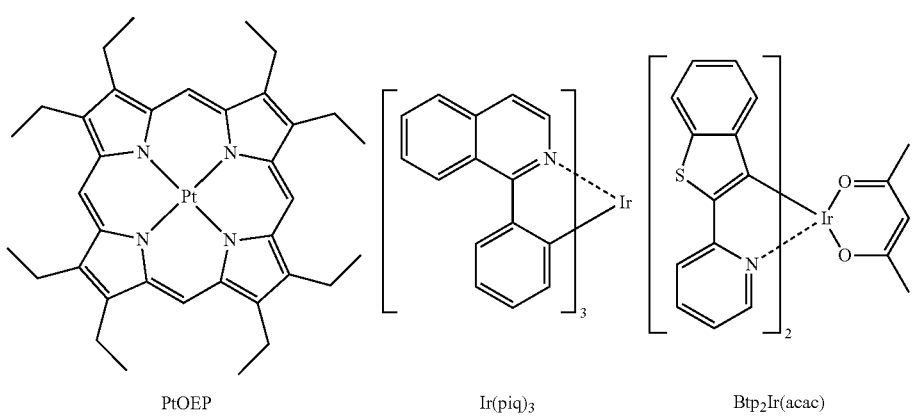

PtOEP            $Ir(piq)_3$            $Btp_2Ir(acac)$

-continued
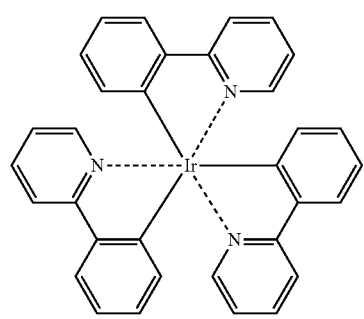
Ir(ppy)₃
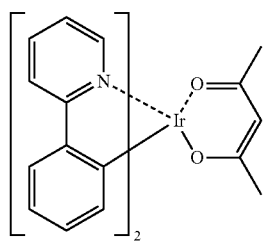
Ir(ppy)₂(acac)
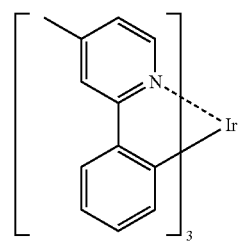
Ir(mpyp)₃
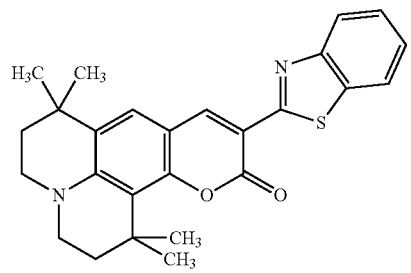
C545T
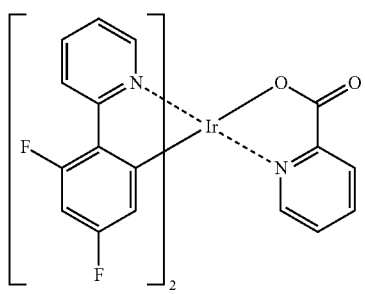
F₂Irpic
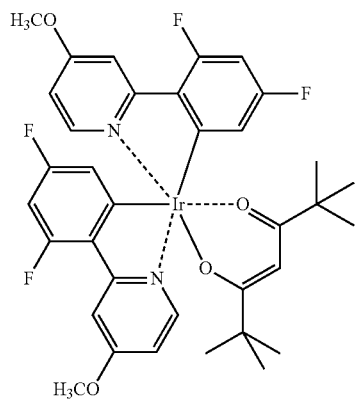
(F₂ppy)₂Ir(tmd)
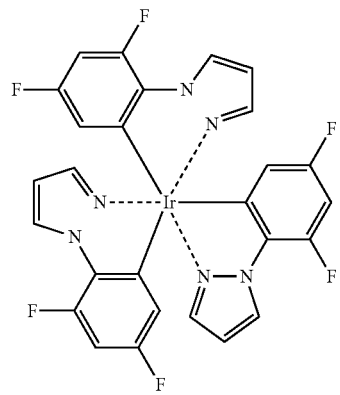
Ir(dfppz)₃
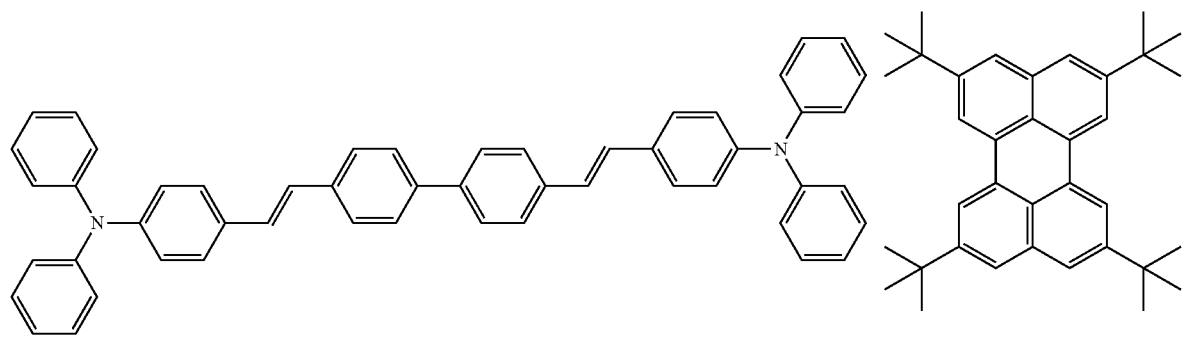
DPAVBi          TBP The amount of the dopant may be in a range of about 0.1 to about 20 parts by weight, for example, about 0.5 to about 12 parts by weight based on 100 parts by weight of the EML-forming material (i.e., the total weight of the host and the dopant). When the amount of the dopant is within the above range, concentration quenching may be substantially prevented.

The thickness of the EML may be in a range of about 100 to about 1,000 Å, for example, about 200 to about 600 Å. When the thickness of the EML is within the above range, the EML may have excellent light-emitting characteristics without a substantial increase in driving voltage.

When the EML includes a phosphorescent dopant, a hole blocking layer (HBL, not shown in FIG. 1) may be formed on the EML in order to prevent diffusion of triplet excitons or holes into the ETL. In this case, the HBL may be formed of any material that is commonly used to form a HBL, without limitation. Examples of such HBL materials include, but are not limited to, oxadiazole derivatives, triazole derivatives, phenathroline derivatives, Balq. and BCP.

The thickness of the HBL may be in a range of about 50 to 1,000 Å, for example, about 100 to about 400 Å. When the thickness of the HBL is within the above range, the HBL may have excellent hole blocking characteristics without a substantial increase in driving voltage.

Then, an ETL may be formed on the HBL or EML by vacuum deposition, spin coating, casting, or the like. When the ETL is formed using vacuum deposition or spin coating, the deposition or coating conditions may be similar to those applied to form the HIL, though the deposition and coating conditions may vary according to the material that is used to form the ETL.

The ETL material may include the heterocyclic compound of Formula 1 described above. In addition to the heterocyclic compound of Formula 1, any known ETL materials may be used to form the ETL. Examples of the ETL material include, but are not limited to, quinoline derivatives, such as tris(8-quinolinolate)aluminum (Alq3), TAZ, and Balq.

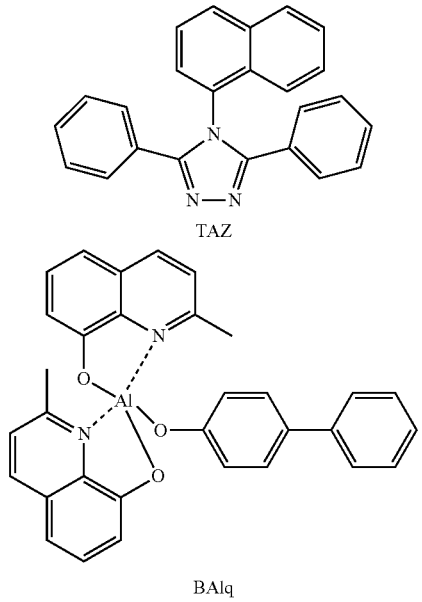

TAZ

BAlq

The thickness of the ETL may be in a range of about 100 to about 1,000 Å, for example, about 100 to about 500 Å. When the ETL has a thickness within the above range, the ETL may have excellent electron transport characteristics without a substantial increase in driving voltage.

In addition, the EIL, which facilitates injection of electrons from the cathode, may be formed on the ETL.

The EIL may include the heterocyclic compound of Formula 1 described above. In addition to the heterocyclic compound of Formula 1, any known EIL materials, such as LiF, NaCl, CsF, $Li_2O$, and BaO, may be used to form the EIL. The deposition or coating conditions for forming the EIL may be similar to those applied to form the HIL, though the deposition and coating conditions may vary according to the material that is used to form the EIL.

The thickness of the EIL may be in a range of about 1 to about 100 Å, for example, about 5 to about 90 Å. When the thickness of the EIL is within the above range, the EIL may have excellent electron injection characteristics without a substantial increase in driving voltage.

Finally, the second electrode may be formed on the EIL using, for example, vacuum deposition, sputtering, or the like. The second electrode may constitute a cathode or an anode. The material for forming the second electrode may include a metal, an alloy, or an electrically conductive compound, materials which a low work function, or a mixture thereof. Examples of such materials may include, but are not limited to, lithium (Li), magnesium (Mg), aluminum (Al), aluminum-lithium (Al-Li), calcium (Ca), magnesium-indium (Mg-In), and magnesium-silver (Mg-Ag). In addition, in order to manufacture a top-emission organic light-emitting device, a transparent cathode formed of a transparent material such as ITO or IZO may be used as the second electrode.

The organic light-emitting device according to the current embodiment of the present invention may be used in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in a flat panel display device having a double-sided screen.

At least one layer of the organic light-emitting device according to the embodiment described above may be formed of the heteroarylamine compound of Formula 1 by using a deposition method or a wet method of coating a solution of the heteroarylamine compound of Formula 1.

Hereinafter, synthesis examples of Compounds 17, 18, 28, 53 and 60 and examples will be described in detail. However, these examples are not intended to limit the purpose and scope of the one or more embodiments of the present invention.

EXAMPLES

Synthesis Example: Synthesis of Compound 17

Synthesis of Intermediate 1

Intermediate 1

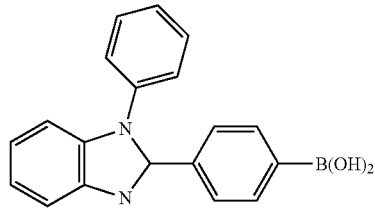

5 g (14 mmol) of 2-(4-bromophenyl)-1-phenyl-benzimidazole, 3.56 g (14 mmol) of bis(pinacolato)diboron, 100 mg (0.14 mmol) of Pd(dppf)$_2$, and 4.12 g (42 mmol) of KOAc were dissolved in 150 mL of dimethylsulfoxide (DMSO), and stirred at 180° C. for 24 hours. The reaction solution was extracted three times with 600 ml of diethylether. The organic phase was collected and dried using magnesium sulfate to evaporate the solvent. The residue was recrystallized with dichloromethane and normal hexane to obtain 3.9 g of Intermediate 1 with a yield of 89%. This compound was identified using high-resolution mass spectroscopy (HR-MS). (calc. 314.1227, found: 314.1495)

Synthesis of Intermediate 2

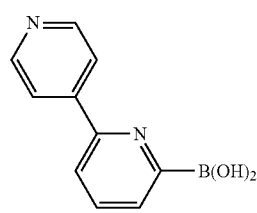

Intermediate 2

Intermediate 2 was synthesized with a yield of 85% in the same manner as that of Intermediate 1, except that [2,4]bipyridinyl was used instead of 2-(4-bromophenyl)-1-phenyl-benzimidazole. This compound was identified using HR-MS. (calc: 200.0757, found: 200.0692)

Synthesis of Intermediate 3

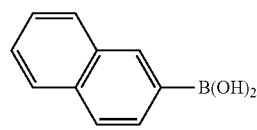

Intermediate 3

Intermediate 3 was synthesized with a yield of 91% in the same manner as that of Intermediate 1, except that 2-bromonaphthalene was used instead of 2-(4-bromophenyl)-1-phenyl-benzimidazole. This compound was identified using HR-MS. (calc: 172.0696, found: 172.0632)

Synthesis of Intermediate 4

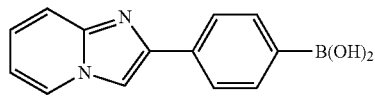

Intermediate 4

Intermediate 4 was synthesized with a yield of 86% in the same manner as that of Intermediate 1, except that 2-(4-bromo-phenyl)-imidazo-[1,2]pyridine was used instead of 2-(4-bromophenyl)-1-phenyl-benzimidazole. This compound was identified using HR-MS. (calc: 162.0601, found: 162.0896)

Synthesis of Intermediate 5

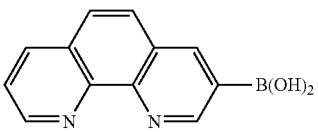

Intermediate 5

Intermediate 4 was synthesized with a yield of 88% in the same manner as that of Intermediate 1, except that 3-bromo-[1,10]phenanthroline was used instead of 2-(4-bromophenyl)-1-phenyl-benzimidazole. This compound was identified using HR-MS. (calc: 222.0852, found: 222.0957)

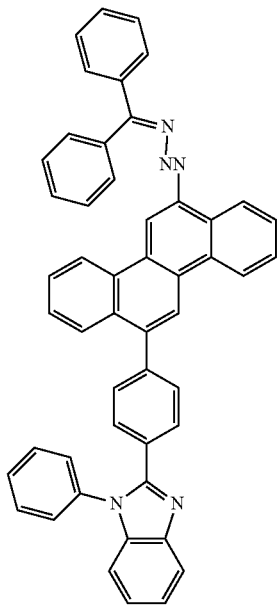

Intermediate 7

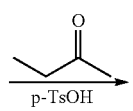

p-TsOH

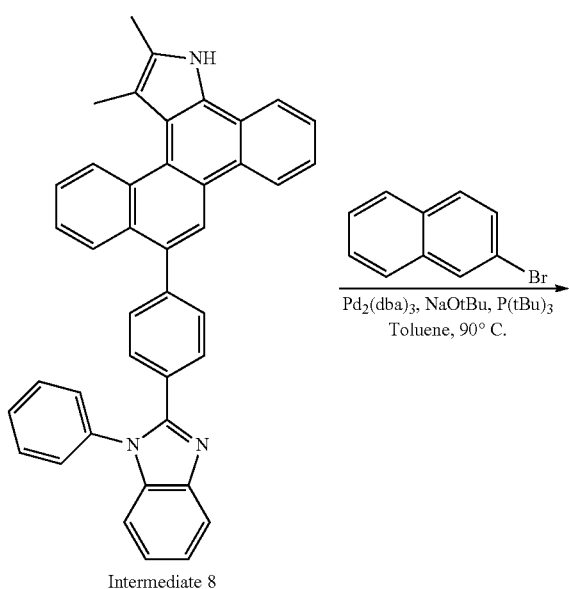

Intermediate 8

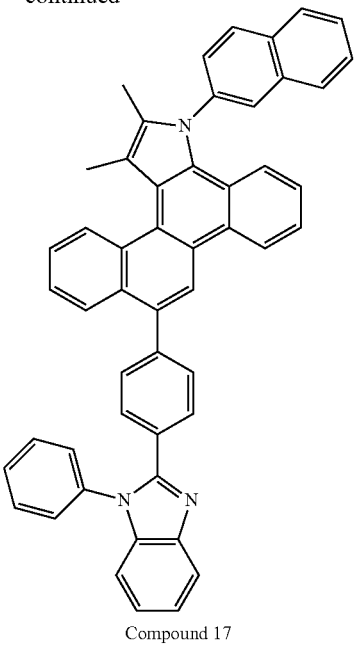

Compound 17

Synthesis of Intermediate 6

3 g (9.5 mmol) of Intermediate 1, 3.7 g (9.5 mmol) of 6,12-dibromo-chrysene, 0.3 g (0.9 mmol) of Pd(PPh$_3$)$_4$, and 3.9 g (28.5 mmol) of K$_2$CO$_3$ were dissolved in 100 ml of a mixed solution THF/H$_2$O (2:1), and stirred at 80° C. for 5 hours. The reaction solution was extracted three times with 600 ml of diethylether. The organic phase was collected and dried using magnesium sulfate to evaporate the solvent. The residue was recrystallized with dichloromethane and normal hexane to obtain 4.2 g of Intermediate 6 with a yield of 76%. This compound was identified using HR-MS. (calc: 574.1045, found: 574.1821)

Synthesis of Intermediate 7

5.7 g (10 mmol) of Intermediate 6, 2.15 g (11 mmol) of benzophenone hydrazone, 1.44 g (15 mmol) of t-BuONa, 45 mg (0.2 mmol) of Pd$_2$(OAc)$_2$, and 95 mg (0.2 mmol) of 2-dicyclohexylphospino-2',4',6'-triisopropylbiphenyl were dissolved in 30 mL of toluene, and stirred at 90° C. for 3 hours. The reaction product was cooled to room temperature. Distilled water was added thereto and extracted twice with 80 mL of diethylether and once with 80 mL of dichloromethane. The organic phase was collected and dried using magnesium sulfate, followed by filtration. The solvent was evaporated to obtain a residue. The residue was separated and purified using silica gel column chromatography to obtain 6.5 g of Intermediate 7 with a yield of 93%. This compound was identified using HR-MS. (calc: 703.2736, found: 703.2682)

Synthesis of Intermediate 8

7 g (20 mmol) of Intermediate 7 and 3.8 g (20 mmol) of p-toluenesulfonic acid monohydrate were dissolved in 50 mL of methylethylketone and stirred at 110° C. for 24 hours. The reaction product was cooled to room temperature. Distilled water was added thereto and extracted twice with 80 mL of diethylether and twice with 80 mL of dichloromethane. The organic phase was collected and dried using magnesium sulfate, followed by filtration. The solvent was evaporated to obtain a residue. The residue was separated and purified using silica gel column chromatography to obtain 3.9 g of Intermediate 8 with a yield of 69%. This compound was identified using HR-MS. (calc: 563.2361, found: 563.2431)

Synthesis of Compound 17

3.9 g (7.0 mmol) of Intermediate 8, 1.7 g (8.4 mmol) of 2-bromo-naphthalene, 2.01 g (21 mmol) of t-BuONa, 130 mg (0.14 mmol) of Pd$_2$(dba)$_3$, and 28 mg (0.14 mmol) of P(t-Bu)$_3$ were dissolved in 30 ml of toluene and stirred at 90° C. for 3 hours in a nitrogen atmosphere. After the reaction was completed, the reaction product was cooled to room temperature and extracted three times with distilled water and 50 ml of diethylether. The organic phase was collected and dried using magnesium sulfate to evaporate the solvent. The residue was separated and purified using silica gel column chromatography to obtain 3.6 g of Compound 17 with a yield of 75%. This compound was identified using HR-MS. (calc: 689.2831, found: 689.2653)

Synthesis Example: Synthesis of Compound 18

Synthesis of Intermediate 9

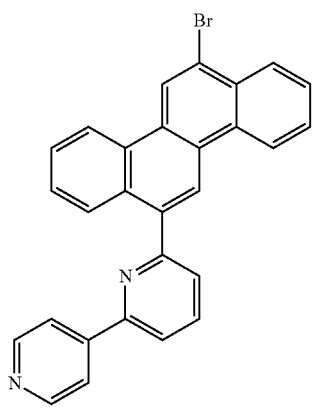

Intermediate 9

Intermediate 9 was synthesized with a yield of 79% in the same manner as that of Intermediate 6, except that Intermediate 2 was used instead of Intermediate 1. This compound was identified using HR-MS. (calc: 460.0575, found: 460.0514)

Synthesis of Intermediate 10

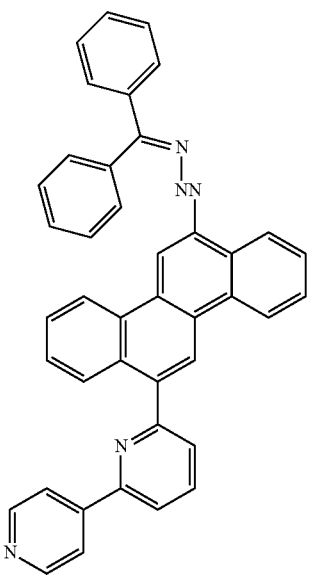

Intermediate 10

Intermediate 10 was synthesized with a yield of 85% in the same manner as that of Intermediate 7, except that Intermediate 9 was used instead of Intermediate 6. This compound was identified using HR-MS. (calc: 589.2266, found: 589.2147)

Synthesis of Intermediate 11

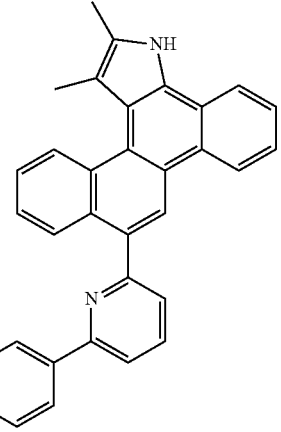

Intermediate 11

Intermediate 11 was synthesized with a yield of 81% in the same manner as that of Intermediate 8, except that Intermediate 10 was used instead of Intermediate 7. This compound was identified using HR-MS. (calc: 449.1892, found: 449.1217)

Synthesis of Compound 18

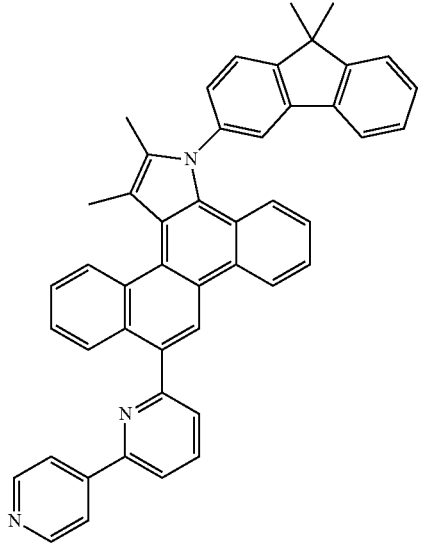

Compound 18

Compound 18 was synthesized with a yield of 83% in the same manner as that of Compound 17, except that Intermediate 11, instead of Intermediate 8, and 3-bromo-9,9-dimethyl-9-fluorene were used. This compound was identified using HR-MS. (calc: 641.2831, found: 641.2281)

Synthesis Example: Synthesis of Compound 28

Synthesis of Intermediate 12

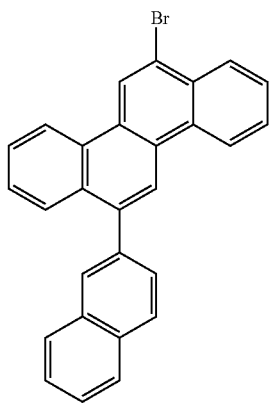

Intermediate 12

Intermediate 12 was synthesized with a yield of 75% in the same manner as that of Intermediate 6, except that Intermediate 3 was used instead of Intermediate 1. This compound was identified using HR-MS. (calc: 432.0514, found: 432.0621)

Synthesis of Intermediate 13

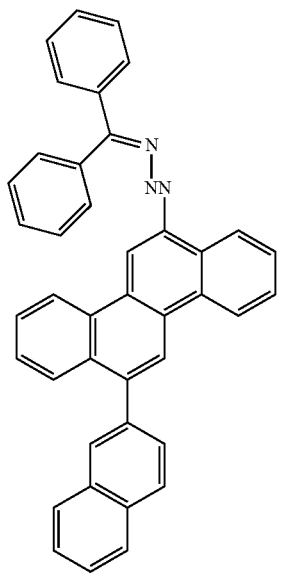

Intermediate 13

Intermediate 13 was synthesized with a yield of 77% in the same manner as that of Intermediate 7, except that Intermediate 12 was used instead of Intermediate 6. This compound was identified using HR-MS. (calc: 561.2205, found: 561.2628)

Synthesis of Intermediate 14

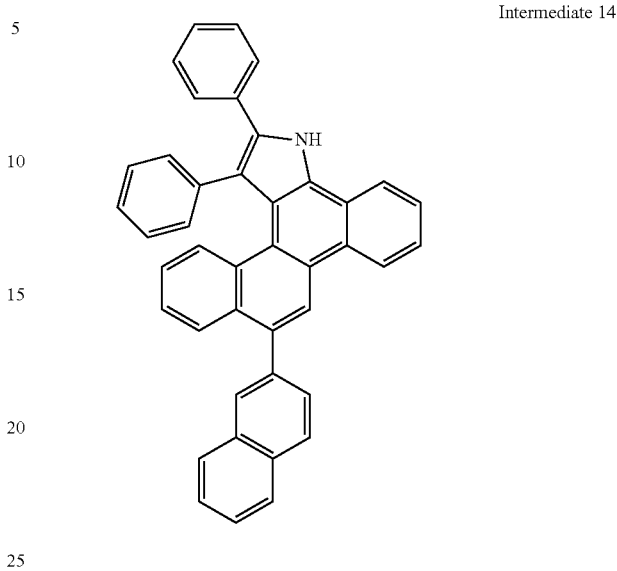

Intermediate 14

Intermediate 13 was synthesized with a yield of 71% in the same manner as that of Intermediate 8, except that Intermediate 13 and 50 mL of benzylphenylketone were used instead of Intermediate 7 and methylethylketone. This compound was identified using HR-MS. (calc: 545.2143, found: 545.2482)

Synthesis of Compound 28

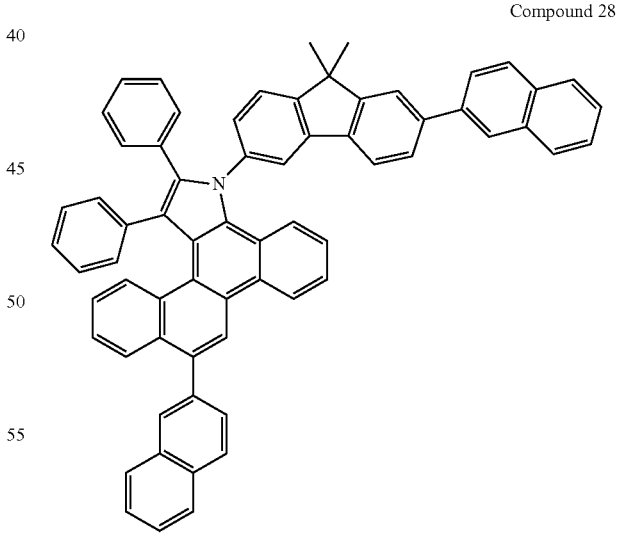

Compound 28

Compound 28 was synthesized with a yield of 86% in the same manner as that of Compound 17, except that Intermediate 14, instead of Intermediate 8, and 6-bromo-9,9-dimethyl-2-naphthalene-2,9-fluorene were used. This compound was identified using HR-MS. (calc: 863.3552, found: 863.3641)

Synthesis Example: Synthesis of Compound 53

Synthesis of Intermediate 15

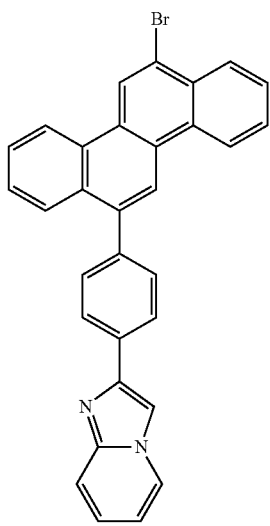

Intermediate 15

Intermediate 15 was synthesized with a yield of 79% in the same manner as that of Intermediate 6, except that Intermediate 4 was used instead of Intermediate 1. This compound was identified using HR-MS. (calc: 498.0732, found: 498.0519)

Synthesis of Intermediate 16

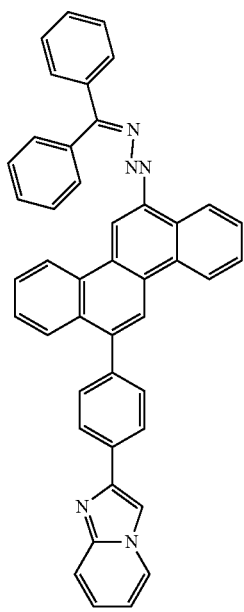

Intermediate 16

Intermediate 16 was synthesized with a yield of 80% in the same manner as that of Intermediate 7, except that Intermediate 15 was used instead of Intermediate 6. This compound was identified using HR-MS. (calc: 627.2413, found: 627.2981)

Synthesis of Intermediate 17

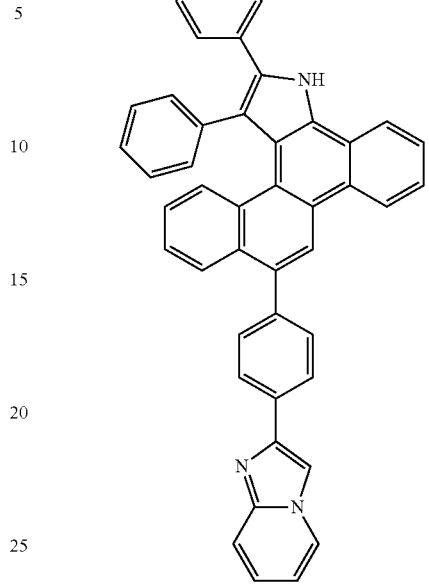

Intermediate 17

Intermediate 17 was synthesized with a yield of 75% in the same manner as that of Intermediate 8, except that Intermediate 14 and 50 mL of benzylphenylketone were used, instead of Intermediate 7 and methylethylketone. This compound was identified using HR-MS. (calc: 611.2361, found: 611.2981)

Synthesis of Compound 53

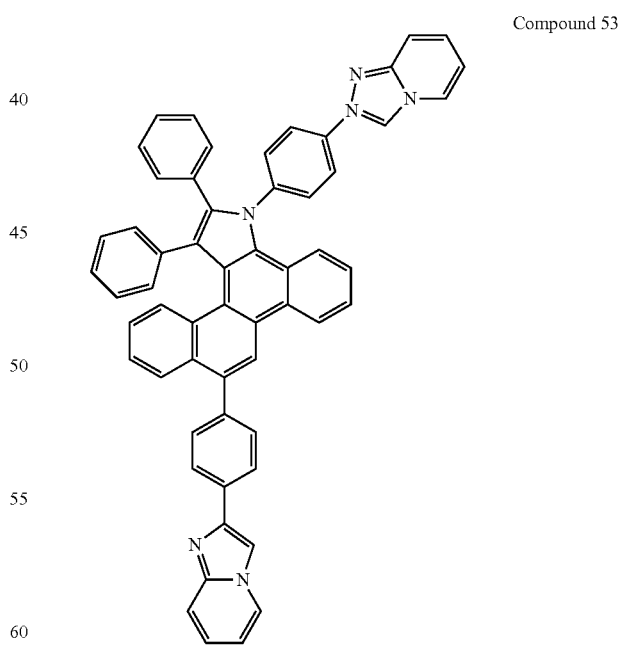

Compound 53

Compound 53 was synthesized with a yield of 88% in the same manner as that of Compound 17, except that Intermediate 17, instead of Intermediate 8, and 2-(4-bromo-phenyl)-imidazo-[1,2]pyridine were used. This compound was identified using HR-MS. (calc: 803.3049, found: 803.3063)

Synthesis Example: Synthesis of Compound 60

Synthesis of Intermediate 18

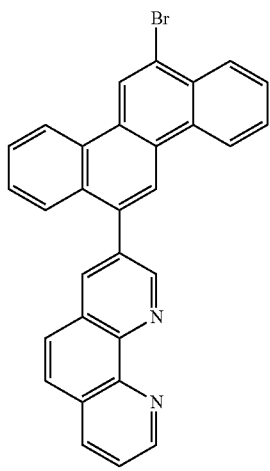

Intermediate 18

Intermediate 18 was synthesized with a yield of 75% in the same manner as that of Intermediate 6, except that Intermediate 5 was used instead of Intermediate 1. This compound was identified using HR-MS. (calc: 484.0575, found: 484.0691)

Synthesis of Intermediate 19

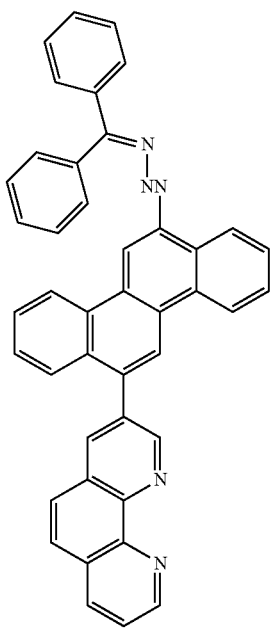

Intermediate 19

Intermediate 19 was synthesized with a yield of 81% in the same manner as that of Intermediate 7, except that Intermediate 18 was used instead of Intermediate 6. This compound was identified using HR-MS. (calc: 613.2266, found: 613.2974)

Synthesis of Intermediate 20

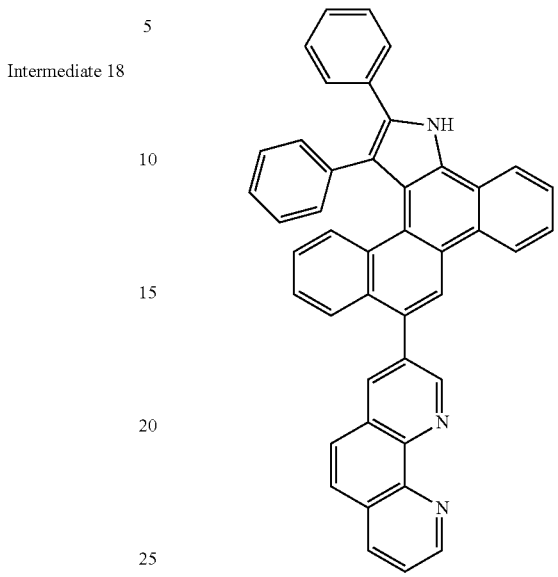

Intermediate 20

Intermediate 20 was synthesized with a yield of 77% in the same manner as that of Intermediate 8, except that Intermediate 19 and 50 mL of benzylphenylketone were used, instead of Intermediate 7 and methylethylketone. This compound was identified using HR-MS. (calc: 597.2205, found: 597.2921)

Synthesis of Compound 60

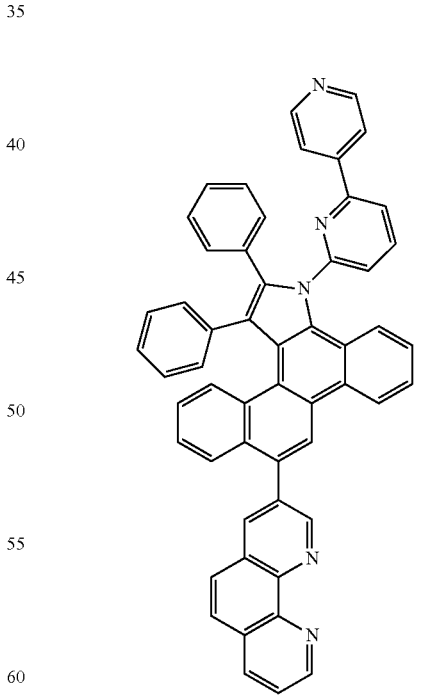

Compound 60

Compound 60 was synthesized with a yield of 81% in the same manner as that of Compound 17, except that Intermediate 20, instead of Intermediate 8, and 6-bromo-[2,4]-bipyridyl were used. This compound was identified using HR-MS. (calc: 751.2736, found: 751.2951)

Example 1

To produce an anode, a corning 15 Ω/cm² (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was mounted on a vacuum deposition device.

Then, first, 2-TNATA, which is a known HIL material, was vacuum-deposited on the glass substrate to form a HIL having a thickness of 600 Å. Then, N,N'-diphenyl-N,N'-bis(1-naphthyl)-1,1'-biphenyl-4,4"-diamine (NPB), which is a known hole transporting compound, was vacuum-deposited on the HIL to form a HTL having a thickness of 300 Å.

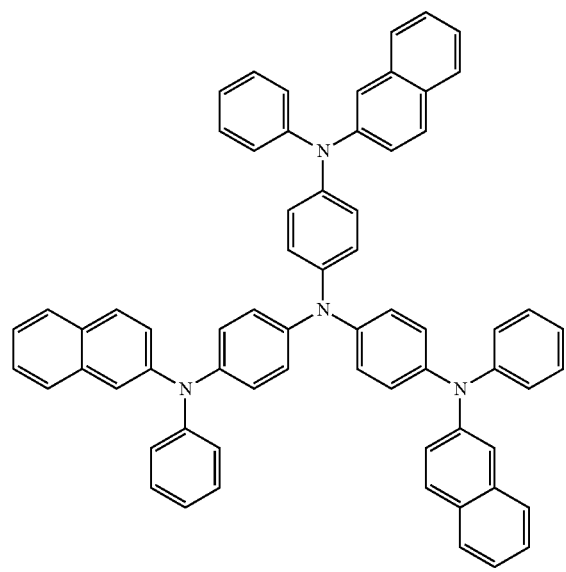

2-TNATA

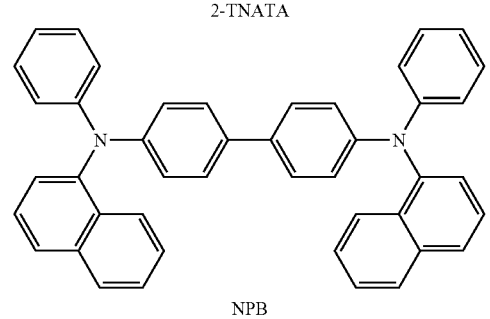

NPB

Then, a green fluorescent host Alq3 and a green fluorescent dopant C545T were simultaneously deposited in a weight ratio of 98:2 on the HTL, to form an EML having a thickness of 300 Å.

Then, Compound 17 was deposited on the EML to form an ETL having a thickness of 300 Å, and then LiF, which is a halogenated alkali metal, was deposited on the ETL to form an EIL having a thickness of 10 Å. Then, Al was vacuum-deposited on the EIL to form a cathode having a thickness of 3000 Å, thereby forming an LiF/Al electrode. As a result, an organic light-emitting device was completely manufactured.

The organic light-emitting device had a driving voltage of 5.93 V at a current density of 50 mA/cm², a high luminosity of 7,950 cd/m², a color coordinate of (0.310, 0.643), and a luminescent efficiency of 15.9 cd/A.

Example 2

An organic light-emitting device was manufactured in the same manner as in Example 1, except that Compound 18 was used, instead of Compound 17, to form the ETL.

Example 3

An organic light-emitting device was manufactured in the same manner as in Example 1, except that Compound 28 was used, instead of Compound 17, to form the ETL.

Example 4

An organic light-emitting device was manufactured in the same manner as in Example 1, except that Compound 53 was used, instead of Compound 17, to form the ETL.

Example 5

An organic light emitting device was manufactured in the same manner as in Example 2, except that Compound 60 was used, instead of Alq3, to form the EML.

Comparative Example 1

An organic light-emitting device was manufactured in the same manner as in Example 1, except that Alq3 was used, instead of Compound 17, to form the ETL.

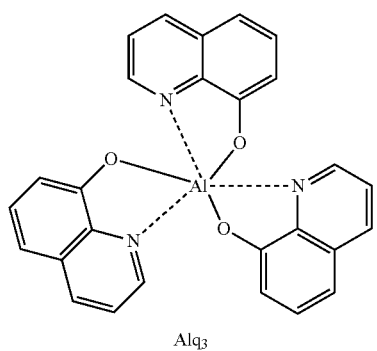

Alq3

The organic light-emitting devices of Examples 1 through 5 had a driving voltage lower by 1 V or greater than the organic light-emitting device of Comparative Example 1, and had higher efficiency and excellent I-V-L characteristics.

TABLE 1

|  | ETL or EML material | Driving Voltage (V) | Current Density (mA/cm²) | Luminance (cd/m²) | Luminescent efficiency (cd/A) | Color coordinates |
| --- | --- | --- | --- | --- | --- | --- |
| Example 1 | Compound 17 | 5.93 | 50 | 7,950 | 15.9 | (0.310, 0.643) |
| Example 2 | Compound 18 | 5.47 | 50 | 8,540 | 17.08 | (0.310, 0.645) |

TABLE 1-continued

|  | ETL or EML material | Driving Voltage (V) | Current Density (mA/cm$^2$) | Luminance (cd/m$^2$) | Luminescent efficiency (cd/A) | Color coordinates |
| --- | --- | --- | --- | --- | --- | --- |
| Example 3 | Compound 28 | 5.75 | 50 | 7,645 | 15.29 | (0.311, 0.643) |
| Example 4 | Compound 53 | 5.35 | 50 | 7,685 | 15.37 | (0.309, 0.643) |
| Example 5 | Compound 60 | 5.83 | 50 | 7,423 | 14.85 | (0.311, 0.644) |
| Comparative Example 1 | Alq3 | 7.11 | 50 | 6,802 | 13.6 | (0.310, 0.643) |

As described above, novel heterocyclic compounds according to the one or more of the above embodiments of the present invention have excellent emission characteristics and charge transporting capability, and thus may be used as an electron transporting material for most color-fluorescent and phosphorescent devices, such as red, green, blue, and white fluorescent and phosphorescent devices, or as a green, blue or white-light emitting material. Thus, an organic light-emitting device with high-efficiency, low-driving voltage, high luminance and long lifespan may be manufactured using the heterocylic compounds.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A heterocyclic compound represented by Formula 1 below:

Formula 1

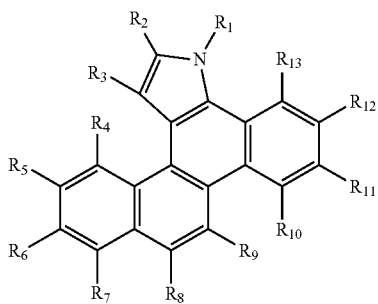

wherein $R_1$ through $R_{13}$ are each independently selected from the group consisting of a hydrogen atom, a deuterium atom, a halogen atom, a cyano group, an amino group, a nitro group, a hydroxyl group, a carboxyl group, a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_3$-$C_{50}$ cycloalkyl group, a substituted or unsubstituted $C_1$-$C_{50}$ alkoxy group, a group represented by $-(Ar_1)_a-(Ar_{11})$, and a group represented by $-N[-(Ar_2)_b-(Ar_{12})][-(Ar_3)_c-(Ar_{13})]$, wherein at least two adjacent groups of $R_1$ through $R_{13}$ are linked to form a saturated or unsaturated ring;

$Ar_1$ through $Ar_3$ are each independently selected from the group consisting of a substituted or unsubstituted $C_1$-$C_{50}$ alkylene group, a substituted or unsubstituted $C_2$-$C_{50}$ alkenylene group, a substituted or unsubstituted $C_5$-$C_{60}$ arylene group, and a substituted or unsubstituted $C_4$-$C_{60}$ heteroarylene group;

$Ar_{11}$, $Ar_{12}$ and $Ar_{13}$ are each independently selected from the group consisting of a substituted or unsubstituted $C_5$-$C_{60}$ aryl group, a substituted or unsubstituted $C_5$-$C_{50}$ aryloxy group, a substituted or unsubstituted $C_5$-$C_{50}$ arylthio group, and a substituted or unsubstituted $C_4$-$C_{60}$ heteroaryl group;

a, b and c are each independently an integer from 0 to 10; and $-(Ar_1)_a-$ groups in $-(Ar_1)_a-(Ar_{11})$ are identical to or different from each other, $-(Ar_2)_b-$ groups in $-N[-(Ar_2)_b-(Ar_{12})][-(Ar_3)_c-(Ar_{13})]$ are identical to or different from each other, and $-(Ar_3)_c-$ groups are identical to or different from each other.

2. A heterocyclic compound of claim 1, wherein $Ar_1$ through $Ar_3$ are each independently selected from the group consisting of a substituted or unsubstituted $C_5$-$C_{20}$ arylene group and a substituted or unsubstituted $C_4$-$C_{20}$ heteroarylene group.

3. A heterocyclic compound of claim 1, wherein $Ar_1$ through $Ar_3$ are each independently selected from the group consisting of a phenylene group, a $C_1$-$C_{10}$ alkyl phenylene group, a di($C_1$-$C_{10}$ alkyl) phenylene group, a naphthylene group, a $C_1$-$C_{10}$ alkyl naphthylene group, a di($C_1$-$C_{10}$ alkyl) naphthylene group, an anthrylene group, a $C_1$-$C_{10}$ alkyl anthrylene group, a di($C_1$-$C_{10}$ alkyl) anthrylene group, a fluorenylene group, a $C_1$-$C_{10}$ alkyl fluorenylene group, a di($C_1$-$C_{10}$ alkyl) fluorenylene group, a $C_6$-$C_{14}$ aryl fluorenylene group, a di($C_6$-$C_{14}$ aryl) fluorenylene group, a pyridylene group, a $C_1$-$C_{10}$ alkyl pyridylene group, a di($C_1$-$C_{10}$ alkyl) pyridylene group, a carbazolylene group, a $C_1$-$C_{10}$ alkyl carbazolylene group, and a di($C_1$-$C_{10}$ alkyl) carbazolylene group.

4. A heterocyclic compound of claim 1, wherein $Ar_1$ through $Ar_3$ are each independently selected from the groups represented by Formulae 2A through 2G below:

Formula 2A

Formula 2B

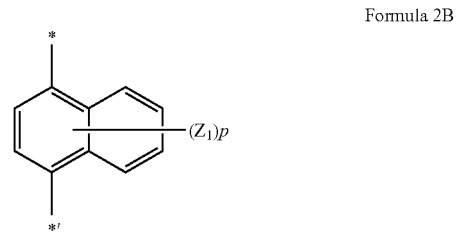

-continued

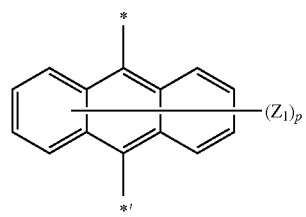
Formula 2C

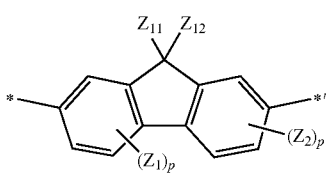
Formula 2D

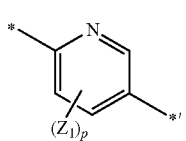
Formula 2E

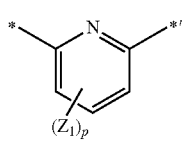
Formula 2F

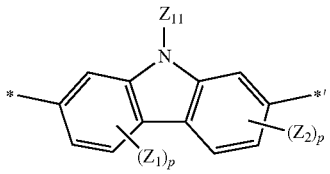
Formula 2G wherein $Z_1$, $Z_2$, $Z_{11}$ and $Z_{12}$ are each independently selected from the group consisting of a hydrogen atom, a deuterium atom, a $C_1$-$C_{10}$ alkyl group, a $C_1$-$C_{10}$ alkoxy group, and a $C_6$-$C_{14}$ aryl group; p is an integer from 1 to 8; * denotes a binding site with $Ar_{11}$, $Ar_{12}$ or $Ar_{13}$; and *' denotes a binding site with a ring of Formula 1, wherein at least two adjacent groups of $Z_1$, $Z_2$, $Z_{11}$ and $Z_{12}$ may be linked to form a saturated or unsaturated ring.

5. A heterocyclic compound of claim 1, wherein $Ar_{11}$, $Ar_{12}$ and $Ar_{13}$ are each independently selected from the group consisting of a substituted or unsubstituted $C_5$-$C_{20}$ aryl group and a substituted or unsubstituted $C_4$-$C_{20}$ heteroaryl group.

6. A heterocyclic compound of claim 1, wherein $Ar_{11}$, $Ar_{12}$ and $Ar_{13}$ are each independently selected from the group consisting of a phenyl group, a $C_1$-$C_{10}$ alkyl phenyl group, a di($C_1$-$C_{10}$ alkyl)phenyl group, a $C_6$-$C_{14}$ aryl phenyl group, a di($C_6$-$C_{14}$ aryl)phenyl group, a naphthyl group, a $C_1$-$C_{10}$ alkyl naphthyl group, a di($C_1$-$C_{10}$ alkyl)naphthyl group, a $C_6$-$C_{14}$ aryl naphthyl group, a di($C_6$-$C_{14}$ aryl)naphthyl group, an anthryl group, a $C_1$-$C_{10}$ alkyl anthryl group, a di($C_1$-$C_{10}$ alkyl)anthryl group, a $C_6$-$C_{14}$ aryl anthryl group, a di($C_6$-$C_{14}$ aryl)anthryl group, a phenanthryl group, a $C_1$-$C_{10}$ alkyl phenanthryl group, a di($C_1$-$C_{10}$ alkyl)phenanthryl group, a $C_6$-$C_{14}$ aryl phenanthryl group, a di($C_6$-$C_{14}$ aryl)phenanthryl group, a fluorenyl group, a $C_1$-$C_{10}$ alkyl fluorenyl group, a di($C_1$-$C_{10}$ alkyl)fluorenyl group, a $C_6$-$C_{14}$ aryl fluorenyl group, a di($C_6$-$C_{14}$ aryl) fluorenyl group, a pyridyl group, a $C_1$-$C_{10}$ alkyl pyridyl group, a di($C_1$-$C_{10}$ alkyl)pyridyl group, a pyrenyl group, a $C_1$-$C_{10}$ alkyl pyrenyl group, a di($C_1$-$C_{10}$ alkyl)pyrenyl group, a $C_6$-$C_{14}$ aryl pyrenyl group, a di($C_6$-$C_{14}$ aryl)pyrenyl group, a phenanthrolinyl group, a $C_1$-$C_{10}$ alkyl phenanthrolinyl group, a di($C_1$-$C_{10}$ alkyl)phenanthiolinyl group, a $C_6$-$C_{14}$ aryl phenanthrolinyl group, a di($C_6$-$C_{14}$ aryl) phenanthrolinyl group, a quinolinyl group, $C_1$-$C_{10}$ alkyl quinolinyl group, a di($C_1$-$C_{10}$ alkyl)quinolinyl group, a $C_6$-$C_{14}$ aryl quinolinyl group, a di($C_6$-$C_{14}$ aryl)quinolinyl group, a benzoxazolyl group, a $C_1$-$C_{10}$ alkyl benzoxazolyl group, a di($C_1$-$C_{10}$ alkyl)benzoxazolyl group, a $C_6$-$C_{14}$ aryl benzoxazolyl group, a di($C_6$-$C_{14}$ aryl)benzoxazolyl group, a benzothiazolyl group, a $C_1$-$C_{10}$ alkyl benzothiazolyl group, a di($C_1$-$C_{10}$ alkyl)benzothiazolyl group, a $C_6$-$C_{14}$ aryl benzothiazolyl group, a di($C_6$-$C_{14}$ aryl)benzothiazolyl group, a benzimidazolyl group, a $C_1$-$C_{10}$ alkyl benzimidazolyl group, a di($C_1$-$C_{10}$ alkyl)benzimidazolyl group, a $C_6$-$C_{14}$ aryl benzimidazolyl group, a di($C_6$-$C_{14}$ aryl)benzimidazolyl group, an imidazolpyridinyl group, a $C_1$-$C_{10}$ alkyl imidazolpyridinyl group, a di($C_1$-$C_{10}$ alkyl) imidazolpyridinyl group, a $C_6$-$C_{14}$ aryl imidazolpyridinyl group, a di($C_6$-$C_{14}$ aryl)imidazolpyridinyl group, an imidazolpyrimidinyl group, a $C_1$-$C_{10}$ alkyl imidazolpyrimidinyl group, a di($C_1$-$C_{10}$ alkyl)imidazolpyrimidinyl group, a $C_6$-$C_{14}$ aryl imidazolpyrimidinyl group, a di($C_6$-$C_{14}$ aryl)imidazolpyrimidinyl group, a carbazolyl group, a $C_1$-$C_{10}$ alkyl carbazolyl group, a di($C_1$-$C_{10}$ alkyl) carbazolyl group, a $C_6$-$C_{14}$ aryl carbazolyl group, and a di($C_6$-$C_{14}$ aryl)carbazolyl group.

7. A heterocyclic compound of claim 1, wherein $Ar_{11}$, $Ar_{12}$, and $Ar_{13}$ are each independently selected from among the groups represented by Formulae 3A through 3O below:

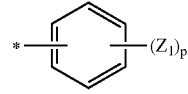
Formula 3A

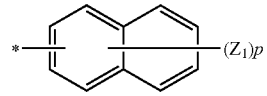
Formula 3B

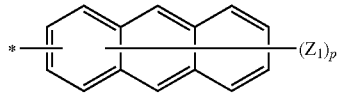
Formula 3C

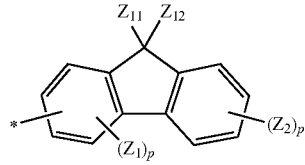
Formula 3D

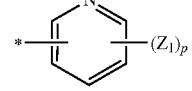
Formula 3E

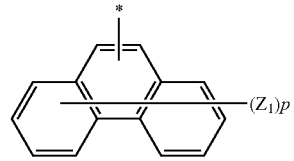
Formula 3F

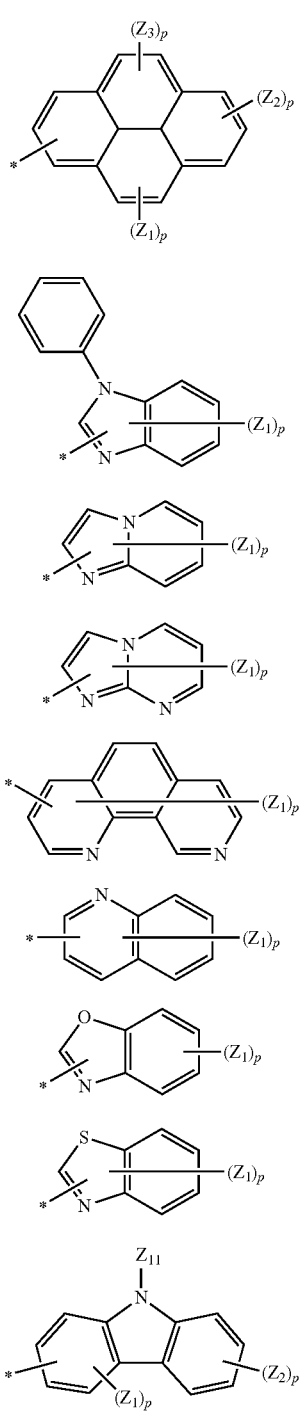

wherein $Z_1$, $Z_2$, $Z_3$, $Z_{11}$ and $Z_{12}$ are each independently selected from the group consisting of a hydrogen atom, a deuterium atom, a $C_1$-$C_{10}$ alkyl group, a $C_1$-$C_{10}$ alkoxy group, and a $C_6$-$C_{14}$ aryl group; p is an integer from 1 to 8; and * denotes a binding site with $Ar_{11}$, $Ar_{12}$ or $Ar_{13}$, wherein at least two adjacent groups of $Z_1$, $Z_2$, $Z_3$, $Z_{11}$ and $Z_{12}$ may be linked to form a saturated or unsaturated ring.

8. A heterocyclic compound of claim 1, wherein a, b, and c are each independently 0, 1, 2 or 3.

9. A heterocyclic compound of claim 1, wherein $R_1$ through $R_{13}$ are each independently selected from the group consisting of a hydrogen atom, a deuterium atom, a halogen atom, a cyano group, an amino group, a nitro group, a hydroxyl group, a substituted or unsubstituted $C_1$-$C_{10}$ alkyl group, a group represented by —$(Ar_1)_a$—$(Ar_{11})$, and a group represented by —$N[—(Ar_2)_b—(Ar_{12})][—(Ar_3)_c—(Ar_{13})]$;

$Ar_1$ through $Ar_3$ are each independently selected from the group consisting of a substituted or unsubstituted $C_5$-$C_{20}$ arylene group and a substituted or unsubstituted $C_4$-$C_{20}$ heteroarylene group;

$Ar_{11}$, $Ar_{12}$ and $Ar_{13}$ are each independently selected from the group consisting of a phenyl group, a $C_1$-$C_{10}$ alkyl phenyl group, a di($C_1$-$C_{10}$ alkyl)phenyl group, a $C_6$-$C_{14}$ aryl phenyl group, a di($C_6$-$C_{14}$ aryl)phenyl group, a naphthyl group, a $C_1$-$C_{10}$ alkyl naphthyl group, a di($C_1$-$C_{10}$ alkyl)naphthyl group, a $C_6$-$C_{14}$ aryl naphthyl group, a di($C_6$-$C_{14}$ aryl)naphthyl group, an anthryl group, a $C_1$-$C_{10}$ alkyl anthryl group, a di($C_1$-$C_{10}$ alkyl)anthryl group, a $C_6$-$C_{14}$ aryl anthryl group, a di($C_6$-$C_{14}$ aryl)anthryl group, a phenanthryl group, a $C_1$-$C_{10}$ alkyl phenanthryl group, a di($C_1$-$C_{10}$ alkyl)phenanthryl group, a $C_6$-$C_{14}$ aryl phenanthryl group, a di($C_6$-$C_{14}$ aryl)phenanthryl group, a fluorenyl group, a $C_1$-$C_{10}$ alkyl fluorenyl group, a di($C_1$-$C_{10}$ alkyl)fluorenyl group, a $C_6$-$C_{14}$ aryl fluorenyl group, a di($C_6$-$C_{14}$ aryl) fluorenyl group, a pyridyl group, a $C_1$-$C_{10}$ alkyl pyridyl group, a di($C_1$-$C_{10}$ alkyl)pyridyl group, a pyrenyl group, a $C_1$-$C_{10}$ alkyl pyrenyl group, a di($C_1$-$C_{10}$ alkyl)pyrenyl group, a $C_6$-$C_{14}$ aryl pyrenyl group, a di($C_6$-$C_{14}$ aryl) pyrenyl group, a phenanthrolinyl group, a $C_1$-$C_{10}$ alkyl phenanthrolinyl group, a di($C_1$-$C_{10}$ alkyl)phenanthrolinyl group, a $C_6$-$C_{14}$ aryl phenanthrolinyl group, a di($C_6$-$C_{14}$ aryl)phenanthrolinyl group, a quinolinyl group, a $C_1$-$C_{10}$ alkyl quinolinyl group, a di($C_1$-$C_{10}$ alkyl)quinolinyl group, a $C_6$-$C_{14}$ aryl quinolinyl group, a di($C_6$-$C_{14}$ aryl)quinolinyl group, a benzoxazolyl group, a $C_1$-$C_{10}$ alkyl benzoxazolyl group, a di($C_1$-$C_{10}$ alkyl)benzoxazolyl group, a $C_6$-$C_{14}$ aryl benzoxazolyl group, a di($C_6$-$C_{14}$ aryl)benzoxazolyl group, a benzothiazolyl group, a $C_1$-$C_{10}$ alkyl benzothiazolyl group, a di($C_1$-$C_{10}$ alkyl) benzothiazolyl group, a $C_6$-$C_{14}$ aryl benzothiazolyl group, a di($C_6$-$C_{14}$ aryl)benzothiazolyl group, a benzimidazolyl group, a $C_1$-$C_{10}$ alkyl benzimidazolyl group, a di($C_1$-$C_{10}$ alkyl)benzimidazolyl group, a $C_6$-$C_{14}$ aryl benzimidazolyl group, a di($C_6$-$C_{14}$ aryl)benzimidazolyl group, an imidazolpyridinyl group, a $C_1$-$C_{10}$ alkyl imidazolpyridinyl group, a di($C_1$-$C_{10}$ alkyl) imidazolpyridinyl group, a $C_6$-$C_{14}$ aryl imidazolpyridinyl group, a di($C_6$-$C_{14}$ aryl)imidazolpyridinyl group, an imidazolpyrimidinyl group, a $C_1$-$C_{10}$ alkyl imidazolpyrimidinyl group, a di($C_1$-$C_{10}$ alkyl)imidazolpyrimidinyl group, a $C_6$-$C_{14}$ aryl imidazolpyrimidinyl group, a di($C_6$-$C_{14}$ aryl)imidazolpyrimidinyl group, a carbazolyl group, a $C_1$-$C_{10}$ alkyl carbazolyl group, a di($C_1$-$C_{10}$ alkyl)carbazolyl group, a $C_6$-$C_{14}$ aryl carbazolyl group, and a di($C_6$-$C_{14}$ aryl)carbazolyl group; and a, b, and c are each independently 0, 1, 2 or 3.

10. A heterocyclic compound of claim 1, wherein the heterocyclic compound is represented by Formula 2 below:

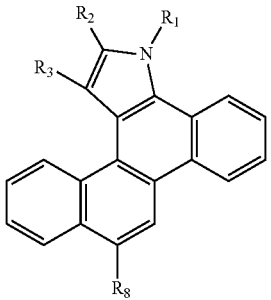

Formula 2 wherein, in Formula 2, $R_1$, $R_2$, $R_3$ and $R_8$ are each independently selected from the group consisting of a substituted or unsubstituted $C_1$-$C_{50}$ alkyl group, a substituted or unsubstituted $C_2$-$C_{50}$ alkenyl group, a substituted or unsubstituted $C_2$-$C_{50}$ alkynyl group, a substituted or unsubstituted $C_3$-$C_{50}$ cycloalkyl group, a substituted or unsubstituted $C_1$-$C_{50}$ alkoxy group, a group represented by —$(Ar_1)_a$—$(Ar_{11})$, and a group represented by —N[—$(Ar_2)_b$—$(Ar_{12})$][—$(Ar_3)_c$—$(Ar_{13})$], wherein at least two adjacent groups of $R_1$ through $R_3$ are linked to form a saturated or unsaturated ring;

$Ar_1$ through $Ar_3$ are each independently selected from the group consisting of a substituted or unsubstituted $C_1$-$C_{50}$ alkylene group, a substituted or unsubstituted $C_2$-$C_{50}$ alkenylene group, a substituted or unsubstituted $C_5$-$C_{60}$ arylene group, and a substituted or unsubstituted $C_4$-$C_{60}$ heteroarylene group;

$Ar_{11}$, $Ar_{12}$ and $Ar_{13}$ are each independently selected from the group consisting of a substituted or unsubstituted $C_5$-$C_{60}$ aryl group, a substituted or unsubstituted $C_5$-$C_{50}$ aryloxy group, a substituted or unsubstituted $C_5$-$C_{50}$ arylthio group, and a substituted or unsubstituted $C_4$-$C_{60}$ heteroaryl group;

a, b and c are each independently an integer from 0 to 10; and

—$(Ar_1)_a$— groups in —$(Ar_1)_a$—$(Ar_{11})$ are identical to or different from each other, —$(Ar_2)_b$— groups in —N[—$(Ar_2)_b$—$(Ar_{12})$][—$(Ar_3)_c$—$(Ar_{13})$] are identical to or different from each other, and —$(Ar_3)_c$— groups are identical to or different from each other.

11. A heterocyclic compound of claim 10, wherein $Ar_1$ through $Ar_3$ are each independently selected from the group consisting of a substituted or unsubstituted $C_5$-$C_{20}$ arylene group and a substituted or unsubstituted $C_4$-$C_{20}$ heteroarylene group.

12. A heterocyclic compound of claim 10, wherein $Ar_1$ through $Ar_3$ are each independently selected from the group consisting of a phenylene group, a $C_1$-$C_{10}$ alkyl phenylene group, a di($C_1$-$C_{10}$ alkyl) phenylene group, a naphthylene group, a $C_1$-$C_{10}$ alkyl naphthylene group, a di($C_1$-$C_{10}$ alkyl) naphthylene group, an anthrylene group, a $C_1$-$C_{10}$ alkyl anthrylene group, a di($C_1$-$C_{10}$ alkyl) anthrylene group, a fluorenylene group, a $C_1$-$C_{10}$ alkyl fluorenylene group, a di($C_1$-$C_{10}$ alkyl) fluorenylene group, a $C_6$-$C_{14}$ aryl fluorenylene group, a di($C_6$-$C_{14}$ aryl) fluorenylene group, a pyridylene group, a $C_1$-$C_{10}$ alkyl pyridylene group, a di($C_1$-$C_{10}$ alkyl) pyridylene group, a carbazolylene group, a $C_1$-$C_{10}$ alkyl carbazolylene group, and a di($C_1$-$C_{10}$ alkyl) carbazolylene group.

13. A heterocyclic compound of claim 10, wherein $Ar_1$ through $Ar_3$ are each independently selected from the groups represented by Formulae 2A through 2G below:

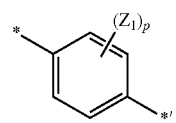

Formula 2A

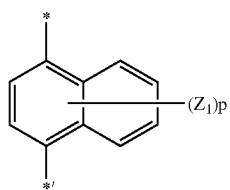

Formula 2B

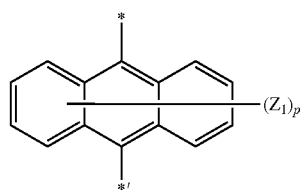

Formula 2C

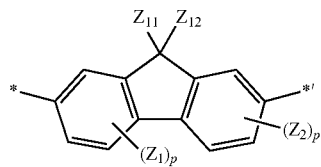

Formula 2D

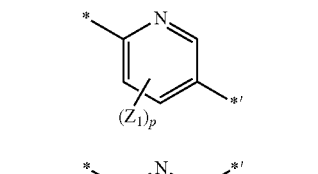

Formula 2E

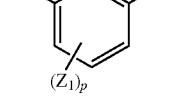

Formula 2F

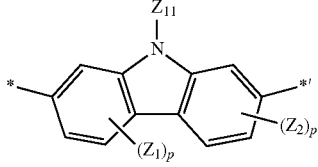

Formula 2G wherein $Z_1$, $Z_2$, $Z_{11}$ and $Z_{12}$ are each independently selected from the group consisting of a hydrogen atom, a deuterium atom, a $C_1$-$C_{10}$ alkyl group, a $C_1$-$C_{10}$ alkoxy group, and a $C_6$-$C_{14}$ aryl group; p is an integer from 1 to 8; * denotes a binding site with $Ar_{11}$, $Ar_{12}$ or $Ar_{13}$; and *' denotes a binding site with a ring of Formula 1, wherein at least two adjacent groups of $Z_1$, $Z_2$, $Z_{11}$ and $Z_{12}$ may be linked to form a saturated or unsaturated ring.

14. A heterocyclic compound of claim 10, wherein $Ar_{11}$, $Ar_{12}$ and $Ar_{13}$ are each independently selected from the group consisting of a substituted or unsubstituted $C_5$-$C_{20}$ aryl group and a substituted or unsubstituted $C_4$-$C_{20}$ heteroaryl group.

15. A heterocyclic compound of claim 10, wherein $Ar_{11}$, $Ar_{12}$ and $Ar_{13}$ are each independently selected from the group consisting of a phenyl group, a $C_1$-$C_{10}$ alkyl phenyl group, a di($C_1$-$C_{10}$ alkyl)phenyl group, a $C_6$-$C_{14}$ aryl phenyl group, a di($C_6$-$C_{14}$ aryl)phenyl group, a naphthyl group, a $C_1$-$C_{10}$ alkyl naphthyl group, a di($C_1$-$C_{10}$ alkyl)naphthyl group, a $C_6$-$C_{14}$ aryl naphthyl group, a di($C_6$-$C_{14}$ aryl)naphthyl group, an anthryl group, a $C_1$-$C_{10}$ alkyl anthryl group, a di($C_1$-$C_{10}$ alkyl)anthryl group, a $C_6$-$C_{14}$ aryl anthryl group, a di($C_6$-$C_{14}$ aryl)anthryl group, a phenanthryl group, a $C_1$-$C_{10}$ alkyl phenanthryl group, a di($C_1$-$C_{10}$ alkyl)phenanthryl group, a $C_6$-$C_{14}$ aryl phenanthryl group, a di($C_6$-$C_{14}$ aryl)phenanthryl group, a fluorenyl group, a $C_1$-$C_{10}$ alkyl fluorenyl group, a di($C_1$-$C_{10}$ alkyl)fluorenyl group, a $C_6$-$C_{14}$ aryl fluorenyl group, a di($C_6$-$C_{14}$ aryl) fluorenyl group, a pyridyl group, a $C_1$-$C_{10}$ alkyl pyridyl group, a di($C_1$-$C_{10}$ alkyl)pyridyl group, a pyrenyl group, a $C_1$-$C_{10}$ alkyl pyrenyl group, a di($C_1$-$C_{10}$ alkyl)pyrenyl group, a $C_6$-$C_{14}$ aryl pyrenyl group, a di($C_6$-$C_{14}$ aryl)pyrenyl group, a phenanthrolinyl group, a $C_1$-$C_{10}$ alkyl phenanthrolinyl group, a di($C_1$-$C_{10}$ alkyl)phenanthrolinyl group, a $C_6$-$C_{14}$ aryl phenanthrolinyl group, a di($C_6$-$C_{14}$ aryl) phenanthrolinyl group, a quinolinyl group, $C_1$-$C_{10}$ alkyl quinolinyl group, a di($C_1$-$C_{10}$ alkyl)quinolinyl group, a $C_6$-$C_{14}$ aryl quinolinyl group, a di($C_6$-$C_{14}$ aryl)quinolinyl group, a benzoxazolyl group, a $C_1$-$C_{10}$ alkyl benzoxazolyl group, a di($C_1$-$C_{10}$ alkyl)benzoxazolyl group, a $C_6$-$C_{14}$ aryl benzoxazolyl group, a di($C_6$-$C_{14}$ aryl)benzoxazolyl group, a benzothiazolyl group, a $C_1$-$C_{10}$ alkyl benzothiazolyl group, a di($C_1$-$C_{10}$ alkyl)benzothiazolyl group, a $C_6$-$C_{14}$ aryl benzothiazolyl group, a di($C_6$-$C_{14}$ aryl)benzothiazolyl group, a benzimidazolyl group, a $C_1$-$C_{10}$ alkyl benzimidazolyl group, a di($C_1$-$C_{10}$ alkyl)benzimidazolyl group, a $C_6$-$C_{14}$ aryl benzimidazolyl group, a di($C_6$-$C_{14}$ aryl)benzimidazolyl group, an imidazolpyridinyl group, a $C_1$-$C_{10}$ alkyl imidazolpyridinyl group, a di($C_1$-$C_{10}$ alkyl) imidazolpyridinyl group, a $C_6$-$C_{14}$ aryl imidazolpyridinyl group, a di($C_6$-$C_{14}$ aryl)imidazolpyridinyl group, an imidazolpyrimidinyl group, a $C_1$-$C_{10}$ alkyl imidazolpyrimidinyl group, a di($C_1$-$C_{10}$ alkyl)imidazolpyrimidinyl group, a $C_6$-$C_{14}$ aryl imidazolpyrimidinyl group, a di($C_6$-$C_{14}$ aryl)imidazolpyrimidinyl group, a carbazolyl group, a $C_1$-$C_{10}$ alkyl carbazolyl group, a di($C_1$-$C_{10}$ alkyl) carbazolyl group, a $C_6$-$C_{14}$ aryl carbazolyl group, and a di($C_6$-$C_{14}$ aryl)carbazolyl group.

16. A heterocyclic compound of claim 10, wherein $Ar_{11}$, $Ar_{12}$, and $Ar_{13}$ are each independently selected from the groups represented by Formulae 3A through 3O below:

Formula 3A
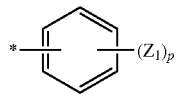

Formula 3B
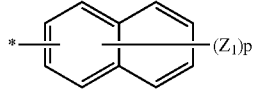

Formula 3C
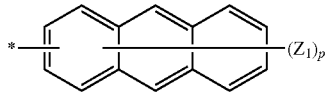

Formula 3D
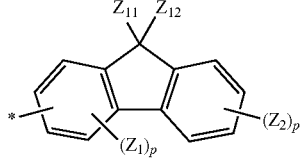

Formula 3E
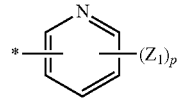

Formula 3F
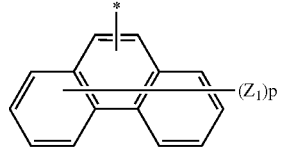

Formula 3G
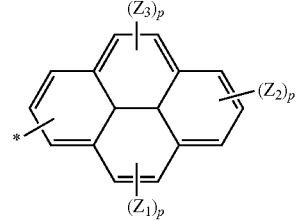

Formula 3H
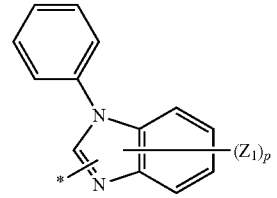

Formula 3I
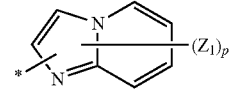

Formula 3J
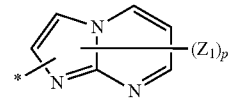

Formula 3K
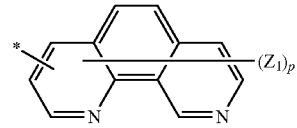

Formula 3L
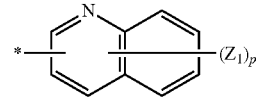

Formula 3M
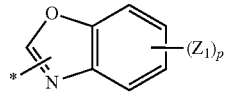

Formula 3N
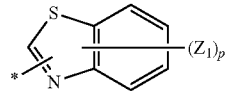

Formula 3O
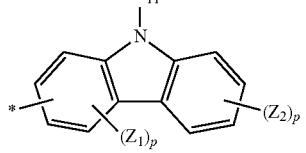

wherein $Z_1$, $Z_2$, $Z_3$, $Z_{11}$ and $Z_{12}$ are each independently selected from the group consisting of a hydrogen atom, a deuterium atom, a $C_1$-$C_{10}$ alkyl group, a $C_1$-$C_{10}$ alkoxy group, and a $C_6$-$C_{14}$ aryl group; p is an integer from 1 to 8; and * denotes a binding site with $Ar_{11}$, $Ar_{12}$ or $Ar_{13}$, wherein at least two adjacent groups of $Z_1$, $Z_2$, $Z_3$, $Z_{11}$ and $Z_{12}$ may be linked to form a saturated or unsaturated ring.

17. A heterocyclic compound of claim 10, wherein a, b, and c are each independently 0, 1, 2 or 3.

18. A heterocyclic compound of claim 10, wherein $R_1$ and $R_8$ are each independently selected from the group consisting of a group represented by —$(Ar_1)_a$—$(Ar_{11})$ and a group represented by —$N[—(Ar_2)_b—(Ar_{12})][—(Ar_3)_c—(Ar_{13})]$; and $R_2$ and $R_3$ are each independently selected from the group consisting of a methyl group and a phenyl group;

$Ar_1$ through $Ar_3$ are each independently selected from the group consisting of a substituted or unsubstituted $C_5$-$C_{20}$ arylene group and a substituted or unsubstituted $C_4$-$C_{20}$ heteroarylene group;

$Ar_{11}$, $Ar_{12}$ and $Ar_{13}$ are each independently selected from the group consisting of a phenyl group, a $C_1$-$C_{10}$ alkyl phenyl group, a di($C_1$-$C_{10}$ alkyl)phenyl group, a $C_6$-$C_{14}$ aryl phenyl group, a di($C_6$-$C_{14}$ aryl)phenyl group, a naphthyl group, a $C_1$-$C_{10}$ alkyl naphthyl group, a di($C_1$-$C_{10}$ alkyl)naphthyl group, a $C_6$-$C_{14}$ aryl naphthyl group, a di($C_6$-$C_{14}$ aryl)naphthyl group, an anthryl group, a $C_1$-$C_{10}$ alkyl anthryl group, a di($C_1$-$C_{10}$ alkyl)anthryl group, a $C_6$-$C_{14}$ aryl anthryl group, a di($C_6$-$C_{14}$ aryl) anthryl group, a phenanthryl group, a $C_1$-$C_{10}$ alkyl phenanthryl group, a di($C_1$-$C_{10}$ alkyl)phenanthryl group, a $C_6$-$C_{14}$ aryl phenanthryl group, a di($C_6$-$C_{14}$ aryl)phenanthryl group, a fluorenyl group, a $C_1$-$C_{10}$ alkyl fluorenyl group, a di($C_1$-$C_{10}$ alkyl)fluorenyl group, a $C_6$-$C_{14}$ aryl fluorenyl group, a di($C_6$-$C_{14}$ aryl) fluorenyl group, a pyridyl group, a $C_1$-$C_{10}$ alkyl pyridyl group, a di($C_1$-$C_{10}$ alkyl)pyridyl group, a pyrenyl group, a $C_1$-$C_{10}$ alkyl pyrenyl group, a di($C_1$-$C_{10}$ alkyl)pyrenyl group, a $C_6$-$C_{14}$ aryl pyrenyl group, a di($C_6$-$C_{14}$ aryl) pyrenyl group, a phenanthrolinyl group, a $C_1$-$C_{10}$ alkyl phenanthrolinyl group, a di($C_1$-$C_{10}$ alkyl)phenanthrolinyl group, a $C_6$-$C_{14}$ aryl phenanthrolinyl group, a di($C_6$-$C_{14}$ aryl)phenanthrolinyl group, a quinolinyl group, a $C_1$-$C_{10}$ alkyl quinolinyl group, a di($C_1$-$C_{10}$ alkyl)quinolinyl group, a $C_6$-$C_{14}$ aryl quinolinyl group, a di($C_6$-$C_{14}$ aryl)quinolinyl group, a benzoxazolyl group, a $C_1$-$C_{10}$ alkyl benzoxazolyl group, a di($C_1$-$C_{10}$ alkyl)benzoxazolyl group, a $C_6$-$C_{14}$ aryl benzoxazolyl group, a di($C_6$-$C_{14}$ aryl)benzoxazolyl group, a benzothiazolyl group, a $C_1$-$C_{10}$ alkyl benzothiazolyl group, a di($C_1$-$C_{10}$ alkyl) benzothiazolyl group, a $C_6$-$C_{14}$ aryl benzothiazolyl group, a di($C_6$-$C_{14}$ aryl)benzothiazolyl group, a benzimidazolyl group, a $C_1$-$C_{10}$ alkyl benzimidazolyl group, a di($C_1$-$C_{10}$ alkyl)benzimidazolyl group, a $C_6$-$C_{14}$ aryl benzimidazolyl group, a di($C_6$-$C_{14}$ aryl)benzimidazolyl group, an imidazolpyridinyl group, a $C_1$-$C_{10}$ alkyl imidazolpyridinyl group, a di($C_1$-$C_{10}$ alkyl) imidazolpyridinyl group, a $C_6$-$C_{14}$ aryl imidazolpyridinyl group, a di($C_6$-$C_{14}$ aryl)imidazolpyridinyl group, an imidazolpyrimidinyl group, a $C_1$-$C_{10}$ alkyl imidazolpyrimidinyl group, a di($C_1$-$C_{10}$ alkyl)imidazolpyrimidinyl group, a $C_6$-$C_{14}$ aryl imidazolpyrimidinyl group, a di($C_6$-$C_{14}$ aryl)imidazolpyrimidinyl group, a carbazolyl group, a $C_1$-$C_{10}$ alkyl carbazolyl group, a di($C_1$-$C_{10}$ alkyl)carbazolyl group, a $C_6$-$C_{14}$ aryl carbazolyl group, and a di($C_6$-$C_{14}$ aryl)carbazolyl group; and a, b, and c are each independently 0, 1, 2 or 3.

19. An organic light-emitting device comprising:
  a first electrode;
  a second electrode disposed opposite to the first electrode; and
  an organic layer disposed between the first electrode and the second electrode, the organic layer comprising a heterocyclic compound of claim 1.

20. The organic light-emitting device of claim 19, wherein the organic layer is selected from the group consisting of an electron injection layer, an electron transport layer, and an emission layer.

* * * * *